United States Patent
Coe et al.

(10) Patent No.: US 7,056,930 B2
(45) Date of Patent: Jun. 6, 2006

(54) 2-AZABICYCLO[3.3.1]NONANE DERIVATIVES

(75) Inventors: Jotham W. Coe, Niantic, CT (US); Stanton McHardy, Coventry, RI (US)

(73) Assignee: Pfizer Inc., New York, NY (US)

( * ) Notice: Subject to any disclaimer, the term of this patent is extended or adjusted under 35 U.S.C. 154(b) by 39 days.

(21) Appl. No.: 10/762,730

(22) Filed: Jan. 22, 2004

(65) Prior Publication Data

US 2004/0204445 A1    Oct. 14, 2004

Related U.S. Application Data

(60) Provisional application No. 60/462,604, filed on Apr. 14, 2003.

(51) Int. Cl.
*A61K 31/439*   (2006.01)
*C07D 221/22*   (2006.01)

(52) U.S. Cl. ....................... 514/299; 546/112
(58) Field of Classification Search ................. 514/299; 546/112

See application file for complete search history.

(56) References Cited

U.S. PATENT DOCUMENTS 2,143,145 A    6/1939   Farnsworth

OTHER PUBLICATIONS

May et al.: "Structures Related to Morphine. II. An Isomer of N-Methylmorphinan" J. Org. Chem., vol. 19, No. 4, 1954, pp. 618-6222, XP002291306, Compound VI.

May: "Structures Related to Morphine. VI. N-Phenylethyl Derivatives of Some Phenyl- And Benz-Morphans" J. Org. Chem., vol. 21, No. 8, 1956, pp. 899-901, XP002291307. Cpd. IIa.

Froimowitz M. et al.: "Phenylmorphans and Analogues: Opioid Receptor Subtype Selectivitiy and Effect of Conformation on Activity", Journal of Medicinal Chemistry, American Chemical Society. Washington, US, vol. 35, No. 9, 1992, pp. 1521-1525, XP002203667, ISSN: 0022-2623 The Whole Document.

Thomas J B et al.: "N-Substituted 9. Beta. -Methyl-5-(3-Hydroxyphenyl)Morphans Are Opioid Receptor Pure Antagonists" Journal of Medicinal Chemistry, American Chemical Society, Washington, US, vol. 41, No. 21, 1998, pp. 4143-4149, XP002203671. ISSN: 0022-2623. The Whole Document.

*Primary Examiner*—Charanjit S. Aulakh
(74) *Attorney, Agent, or Firm*—Gregg C. Benson; Arlene K. Musser

(57) ABSTRACT

The subject invention relates to 2-azabicyclo[3.3.1]nonane derivatives, pharmaceutical compositions comprising such derivatives and methods of using such derivatives to treat disease states, disorders and conditions mediated by opioid receptors. The subject invention also particularly relates to using such derivatives to treat certain disorders and conditions, for example irritable bowel syndrome, drug addiction, including alcohol addiction, depression, anxiety, schizophrenia and eating disorders, among others, as are more fully described herein.

22 Claims, No Drawings

2-AZABICYCLO[3.3.1]NONANE DERIVATIVES

FIELD OF THE INVENTION

The subject invention relates to 2-azabicyclo[3.3.1] nonane derivatives, pharmaceutical compositions comprising such derivatives and methods of using such derivatives to treat disease states, disorders and conditions mediated by opioid receptors. The subject invention also particularly relates to using such derivatives to treat certain disorders and conditions, for example irritable bowel syndrome, drug addiction, including alcohol addiction, depression, anxiety, schizophrenia and eating disorders, among others as will be more fully described herein.

BACKGROUND OF THE INVENTION

The compounds of the subject invention bind to opioid receptors (e.g. mu, kappa and delta opioid receptors). Compounds that bind to such receptors are likely to be useful in the treatment of diseases modulated by opioid receptors, for example irritable bowel syndrome; constipation; nausea; vomiting; and pruritic dermatoses, such as allergic dermatitis and atopy in animals and humans. Compounds that bind to opioid receptors have also been indicated in the treatment of eating disorders, opioid overdoses, depression, anxiety, schizophrenia, alcohol addiction, including alcohol abuse and dependency, sexual dysfunction, shock, stroke, spinal damage and head trauma.

Certain 4-arylpiperidine-based compounds are disclosed in European patent applications EP 287339, EP 506468 and EP 506478 as opioid receptor binding agents. In addition, International Patent Application WO 95/15327 discloses azabicycloalkane derivatives useful as neuroleptic agents. 3-Azabicyclo[3.1.0] hexane derivatives useful as opioid receptor agents are also disclosed in WO 00/39089.

SUMMARY OF THE INVENTION

The subject invention is directed to compounds of formula I:

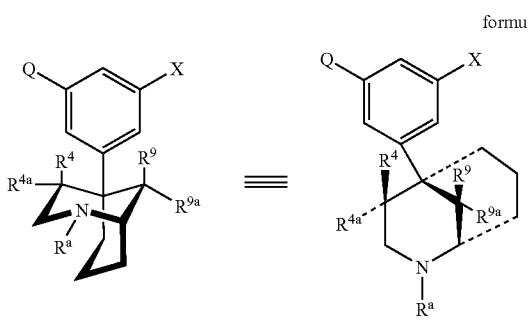

formula I wherein $R^a$ is H or a

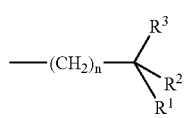

R group;

Wherein X is H, halogen, —CN, —C≡C—$R^{3a}$ or a —$C_1$-$C_4$ alkyl group optionally substituted with from one to three halogen atoms;

Q is H, halogen, a $C_1$-$C_6$ alkyl, —CN, —$NH_2$, —NH ($C_1$-$C_4$ alkyl), —N($C_1$-$C_4$ alkyl)($C_1$-$C_4$ alkyl), —C(=O) $NH_2$, —C(=O)NH($C_1$-$C_4$ alkyl), —C(=O)N($C_1$-$C_4$ alkyl) ($C_1$-$C_4$ alkyl), —NHC(=O)H, —NHC(=O)$R^8$, or —NHS (=O)$_2R^8$;

$R^1$ and $R^2$ are independently H, a $C_1$-$C_6$ alkyl, —$(CH_2)_j$-aryl, —$(CH_2)_j$-heteroary, wherein said alkyl, —$(CH_2)_j$-aryl or —$(CH_2)_j$-heteroaryl group is optionally substituted with one or more $R^{10}$ groups, or with the carbon to which $R^1$ and $R^2$ are attached, $R^1$ and $R^2$ form a $C_3$-$C_7$ carbocyclic or 4- to 7-membered heterocyclic group, wherein said heterocyclic group comprises from one to three heteroatoms selected from the group consisting of O, S and N and said carbocyclic or heterocyclic group optionally contains a —C(=O) group or optionally contains one or more double bonds and is optionally fused to or substituted with a $C_6$-$C_{14}$ aryl or a 5–14 membered heteroaryl group; wherein said $C_3$-$C_7$ carbocyclic or 4- to 7-membered heterocyclic group formed by $R^1$ and $R^2$ may optionally be substituted with from one to three $R^{10}$ groups, and said optionally fused or substituted aryl or heteroaryl group may each optionally independently be substituted with from one to six $R^{10}$ groups;

$R^{10}$ groups are independently selected from $R^{11}$, H, halogen, —$OR^{11}$, —$NO_2$, —CN, —$C_1$-$C_6$ alkyl, —$C_3$-$C_6$ cycloalkyl, —$C(R^3)R^{10a}R^{10b}$, aryl optionally substituted with from 1 to 3 $R^3$ groups, —$(CH_2)_v$—$NR^{11}R^{12}$, —$NR^{11}C$ (=O)$R^{12}$, —C(=O)$NR^{11}R^{12}$, —OC(=O)$R^{11}$, —C(=O) $OR^{11}$, C(=O)$R^{11}$, —$NR^{11}C(=O)OR^{12}$, —$NR^{11}C(=O)$ $NR^{12}R^{13}$, —$NR^{12}S(=O)_2R^{11}$, —$NR^{11}S(=O)_2NR^{12}R^{13}$, and —S(=O)$_2R^{11}$;

$R^3$ is absent or is H, —$C_1$-$C_4$ alkyl, which optionally contains one or two unsaturated bonds, —OH, —O($C_1$-$C_4$) alkyl, —($C_1$-$C_4$)alkylOH, —$(CH_2)_n$—$NR^{10a}R^{10b}$, —$(CH_2)_n$ —NHC(=O)($C_1$-$C_4$ alkyl), —$(CH_2)_n$—$NO_2$, —$(CH_2)_n$—C≡N, —$(CH_2)_n$—C(=O)$NH_2$, —$(CH_2)_n$—C (=O)NH($C_1$-$C_4$ alkyl) or —$(CH_2)_v$—C(=O)$NR^{10a}R^{10b}$;

$R^{3a}$ is H or $C_1$-$C_6$ alkyl which may be optionally substituted with one or more halogen groups;

each $R^4$, $R^{4a}$, $R^9$ and $R^{9a}$ is independently H, —$C_1$-$C_4$ alkyl or —O—$C_1$-$C_4$ alkyl;

each $R^8$, $R^{11}$, $R^{12}$ and $R^{13}$ is independently selected from H, —$C_1$-$C_6$ alkyl, $C_3$-$C_6$ cycloalkyl, aryl, —$(C_2$-$C_4$ alkyl)—O—($C_1$-$C_4$alkyl), aryl, —$(CH_2)_m$—$NR^{14}R^{15}$, or a 4- to 7-membered heterocyclic group, or where any two groups selected from $R^{11}$, $R^{12}$ and $R^{13}$ can form a heterocyclic ring with the atom to which they are attached, wherein said heterocyclic group or said heterocyclic ring is optionally substituted with at least one $C_1$-$C_4$ alkyl group;

each $R^{10a}$ and $R^{10b}$ is independently selected from H, —$C_1$-$C_4$ alkyl; or, independently in each instance of —C($R^3$)$R^{10a}R^{10b}$, $R^{10a}$ and $R^{10b}$ connect to form a $C_3$-$C_7$ carbocyclic ring or a 4–7 membererd heterocyclic ring or in each instance of —$(CH_2)_v$—C(=O)$NR^{10a}$, $R^{10b}$, $R^{10a}$ and $R^{10b}$ connect to form a 4–7 membererd heterocyclic ring;

$R^{14}$ and $R^{15}$ are independently H, $C_1$-$C_6$ alkyl or together may form a 4- to 7-membered carbocyclic or heterocyclic ring;

j is in each instance independently an integer from 0 to 5;
m is 0 or an independently variable integer 2 or greater;
n is in each instance independently an integer from 0 to 5;
v is in each instance independently an integer from 0 to 5;
and pharmaceutically acceptable salts thereof, with the provisos that a) when $R^a$ is

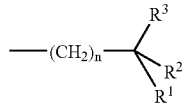

and n is 0, and when the carbon to which $R^1$, $R^2$ and $R^4$ are bound is $sp^3$ hybridized (i.e., "saturated"), then none of $R^1$, $R^2$ and $R^4$ can be a heteroatom or contain a heteroatom which is directly linked to the carbon of said

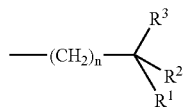

group;

b) $R^8$ cannot be H when part of a —NHS(=O)$_2R^8$ group, $R^{11}$ cannot be H when part of a —NR$^{12}$S(=O)$_2R^{11}$ and —S(=O)$_2R^{11}$; and c) v of —(CH$_2$)$_v$— cannot be 1 when said methylene unit is connected to N, O or S.

Preferred embodiments of the subject invention include compounds according to formula I, above, Q is —C(=O)NH$_2$ or —NHS(=O$_2$)R$^8$, more preferably —NHS(=O$_2$)R$^8$, wherein $R^8$ is CH$_3$, —(CH$_2$)$_2$—O—CH$_3$ or -4-(1-methylimidazole). Preferably, X is selected from H or F.

In other preferred embodiments of the subject invention, including the above-described preferred embodiments, $R^a$ is

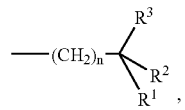

n is 1–3, more preferably 1.

In still further aspects of the subject invention, $R^1$ and $R^2$ taken together with the carbon to which they are attached, are preferably selected from cyclobutane, cyclopentane, cyclohexane, indane-2-yl, 1,2,3,4-tetrahydronaphth-2-yl, wherein each may be substituted with $R^{10}$ groups as previously described.

In still other preferred embodiments, $R^3$ is H, OH, —NH(=O)—CH$_3$, —C(=O)NH$_2$, —CH$_2$OH or OCH$_3$, more preferably OH.

In still other preferred embodiments of the subject invention, each $R^4$ and $R^9$ is independently H or —C$_1$–C$_4$ alkyl, more preferably H or methyl. Even more preferably, $R^4$ or $R^9$ are both methyl.

In more preferred embodiments of the subject invention, in the above formula I, Q is —C(=O)NH$_2$, —NHSO$_2$CH$_3$ or —NHSO$_2$CH$_2$CH$_2$OCH$_3$ and X is H.

Preferred embodiments of the invention also include compounds, and therapeutic methods and pharmaceutical compositions comprising such compounds, where $R^a$ is a

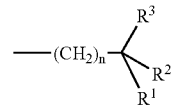

group; and $R^1$ and $R^2$ taken together with the carbon to which they are attached form a cyclobutane, cyclopentane, cyclohexane, indane-2-yl or 1,2,3,4-tetrahydronaphth-2-yl which may be unsubstituted or substituted with $R^{10}$ groups as described above. In such embodiments, $R^3$ is more preferably H, —OH, —NH(=O)—CH$_3$, —C(=O)NH$_2$, —CH$_2$OH or —OCH$_3$. Most preferably in such embodiments $R^3$ is OH. In the preferred embodiments described above, n is preferably 1–3, more preferably 1.

In the subject invention, the following compounds of formula I are also preferred:

3-(2-Ethyl-2-aza-bicyclo[3.3.1]non-5-yl)-benzamide;
3-(2-Cyclopropylmethyl-2-aza-bicyclo[3.3.1]non-5-yl)-benzamide;
3-(2-lsobutyl-2-aza-bicyclo[3.3.1]non-5-yl)-benzamide;
3-[2-(3-Methyl-butyl)-2-aza-bicyclo[3.3.1]non-5-yl]-benzamide;
3-(2-Pentyl-2-aza-bicyclo[3.3.1]non-5-yl)-benzamide;
3-[2-(1H-Pyrrol-2-ylmethyl)-2-aza-bicyclo[3.3.1]non-5-yl]-benzamide;
3-[2-(1H-lmidazol-2-ylmethyl)-2-aza-bicyclo[3.3.1]non-5-yl]-benzamide;
3-[2-(1-Hydroxy-cyclobutylmethyl)-2-aza-bicyclo[3.3.1]non-5-yl]-benzamide;
3-(2-Hexyl-2-aza-bicyclo[3.3.1]non-5-yl)-benzamide;
3-[2-(2-Ethyl-butyl)-2-aza-bicyclo[3.3.1]non-5-yl]-benzamide;
3-[2-(1-Methyl-1H-pyrrol-2-ylmethyl)-2-aza-bicyclo[3.3.1]non-5-yl]-benzamide;
3-(2-Thiophen-3-ylmethyl-2-aza-bicyclo[3.3.1]non-5-yl)-benzamide;
3-(2-Thiazol-2-ylmethyl-2-aza-bicyclo[3.3.1]non-5-yl)-benzamide;
3-[2-(1-Hydroxymethyl-cyclobutylmethyl)-2-aza-bicyclo[3.3.1]non-5-yl]-benzamide;
3-(2-Heptyl-2-aza-bicyclo[3.3.1]non-5-yl)-benzamide;
3-(2-Phenethyl-2-aza-bicyclo[3.3.1]non-5-yl)-benzamide;
3-[2-(3-Cyclopentyl-propyl)-2-aza-bicyclo[3.3.1]non-5-yl]-benzamide;
3-[2-(2-Ethyl-hexyl)-2-aza-bicyclo[3.3.1]non-5-yl]-benzamide;
3-[2-Octyl-2-aza-bicyclo[3.3.1]non-5-yl)-benzam ide;
3-[2-(3-Phenyl-prop-2-ynyl)-2-aza-bicyclo[3.3.1]non-5-yl]-benzamide;
3-[2-(3-Phenyl-propyl)-2-aza-bicyclo[3.3.1]non-5-yl]-benzamide;
3-[2-(4-Methoxy-benzyl)-2-aza-bicyclo[3.3.1]non-5-yl]-benzamide;
3-[2-(3-Cyclohexyl-propyl)-2-aza-bicyclo[3.3.1]non-5-yi]-benzamide;
3-{2-[3-(1-Hydroxy-cyclopentyl)-propyl]-2-aza-bicyclo[3.3.1]non-5-yl}-benzamide;
3-[2-(1H-Indol-3-ylmethyl)-2-aza-bicyclo[3.3.1]non-5-yl]-benzamide;
3-(2-Benzofuran-2-ylmethyl-2-aza-bicyclo[3.3.1]non-5-yl)-benzamide;
3-(2-Indan-2-ylmethyl-2-aza-bicyclo[3.3.1]non-5-yl)-benzamide;

3-(2-Naphthalen-2-ylmethyl-2-aza-bicyclo[3.3.1]non-5-yl)-benzamide;
3-(2-Naphthalen-1-ylmethyl-2-aza-bicyclo[3.3.1]non-5-yl)-benzamide;
3-{2-[3-(1-Hydroxy-cyclohexyl)-propyl]-2-aza-bicyclo[3.3.1]non-5-yl}-benzamide;
3-{2-[3-(1-Hydroxymethyl-cyclopentyl)-propyl]-2-aza-bicyclo[3.3.1]non-5-yl}-benzamide;
3-(2-Quinolin-4-ylmethyl-2-aza-bicyclo[3.3.1]non-5-yl)-benzamide;
3-(2-Quinolin-3-ylmethyl-2-aza-bicyclo[3.3.1]non-5-yl)-benzamide;
3-[2-(4-Chloro-2-fluoro-benzyl)-2-aza-bicyclo[3.3.1]non-5-yl]-benzamide;
3-[2-(1-Methyl-1H-indol-3-ylmethyl)-2-aza-bicyclo[3.3.1]non-5-yl]-benzamide;
3-[2-(1,2,3,4-Tetrahydro-naphthalen-2-ylmethyl)-2-aza-bicyclo[3.3.1]non-5-yl]-benzamide;
3-[2-(3-Phenyl-cyclobutylmethyl)-2-aza-bicyclo[3.3.1]non-5-yl]-benzamide;
3-[2-(2-Hydroxy-indan-2-ylmethyl)-2-aza-bicyclo[3.3.1]non-5-yl]-benzamide;
3-[2-(2-Phenethyloxy-ethyl)-2-aza-bicyclo[3.3.1]non-5-yl]-benzamide;
3-[2-(4-Hydroxy-naphthalen-1-ylmethyl)-2-aza-bicyclo[3.3.1]non-5-yl]-benzamide;
3-[2-(3-Indan-2-yl-propyl)-2-aza-bicyclo[3.3.1]non-5-yl]-benzamide;
3-[2-(4-Pyrrolidin-1-yl-benzyl)-2-aza-bicyclo[3.3.1]non-5-yl]-benzamide;
3-[2-(2-Hydroxy-1,2,3,4-tetrahydro-naphthalen-2-ylmethyl)-2-aza-bicyclo[3.3.1]non-5-yl]-benzamide;
3-[2-(1-Hydroxy-3-phenyl-cyclobutylmethyl)-2-aza-bicyclo[3.3.1]non-5-yl]-benzamide;
3-[2-(3-Methyl-benzo[b]thiophen-2-ylmethyl)-2-aza-bicyclo[3.3.1]non-5-yl]-benzamide;
3-{2-[2-(4-Chloro-phenyl)-2-cyano-ethyl]-2-aza-bicyclo[3.3.1]non-5-yl}-benzamide;
3-(2-Biphenyl-4-ylmethyl-2-aza-bicyclo[3.3.1]non-5-yl)-benzamide;
3-[2-(3-Trifluoromethoxy-benzyl)-2-aza-bicyclo[3.3.1]non-5-yl]-benzamide;
3-{2-[3-(2-Hydroxy-indan-2-yl)-propyl]-2-aza-bicyclo[3.3.1]non-5-yl}-benzamide;
3-[2-(9H-Fluoren-2-ylmethyl)-2-aza-bicyclo[3.3.1]non-5-yl]-benzamide;
3-[2-(3-Phenoxy-benzyl)-2-aza-bicyclo[3.3.1]non-5-yl]-benzamide;
3-[2-(4-Dimethylamino-naphthalen-1-ylmethyl)-2-aza-bicyclo[3.3.1]non-5-yl]-benzamide;
N-[3-(2-Ethyl-2-aza-bicyclo[3.3.1]non-5-yl)-phenyl]-methanesulfonamide;
N-[3-(2-Cyclopropylmethyl-2-aza-bicyclo[3.3.1]non-5-yl)-phenyl]-methanesulfonamide;
N-[3-(2-Isobutyl-2-aza-bicyclo[3.3.1]non-5-yl)-phenyl]-methanesulfonamide;
N-{3-[2-(3-Methyl-butyl)-2-aza-bicyclo[3.3.1]non-5-yl]-phenyl}-methanesulfonamide;
N-[3-(2-Pentyl-2-aza-bicyclo[3.3.1]non-5-yl)-phenyl]-methanesulfonamide;
N-{3-[2-(1H-Pyrrol-2-ylmethyl)-2-aza-bicyclo[3.3.1]non-5-yl]-phenyl}-methanesulfonamide;
N-{3-[2-(1H-Imidazol-2-ylmethyl)-2-aza-bicyclo[3.3.1]non-5-yl]-phenyl}-methanesulfonamide;
N-{3-[2-(1-Hydroxy-cyclobutylmethyl)-2-aza-bicyclo[3.3.1]non-5-yl]-phenyl}-methanesulfonamide;
N-[3-(2-Hexyl-2-aza-bicyclo[3.3.1]non-5-yl)-phenyl]-methanesulfonamide;
N-{3-[2-(2-Ethyl-butyl)-2-aza-bicyclo[3.3.1]non-5-yl]-phenyl}-methanesulfonamide;
N-{3-[2-(1-Methyl-1H-pyrrol-2-ylmethyl)-2-aza-bicyclo[3.3.1]non-5-yl]-phenyl}methanesulfonamide;
N-[3-(2-Thiophen-3-ylmethyl-2-aza-bicyclo[3.3.1]non-5-yl)-phenyl]-methanesulfonamide;
N-[3-(2-Thiazol-2-ylmethyl-2-aza-bicyclo[3.3.1]non-5-yl)-phenyl]-methanesulfonamide;
N-{3-[2-(1-Hydroxymethyl-cyclobutylmethyl)-2-aza-bicyclo[3.3.1]non-5-yl]-phenyl}-methanesulfonamide;
N-[3-(2-Heptyl-2-aza-bicyclo[3.3.1]non-5-yl)-phenyl]-methanesulfonamide;
N-[3-(2-Phenethyl-2-aza-bicyclo[3.3.1]non-5-yl)-phenyl]-methanesulfonamide;
N-{3-[2-(3-Cyclopentyl-propyl)-2-aza-bicyclo[3.3.1]non-5-yl]-phenyl}-methanesulfonamide;
N-{3-[2-(2-Ethyl-hexyl)-2-aza-bicyclo[3.3.1]non-5-yl]-phenyl)-methanesulfonamide;
N-[3-(2-Octyl-2-aza-bicyclo[3.3.1]non-5-yl)-phenyl]-methanesulfonamide;
N-{3-[2-(3-Phenyl-prop-2-ynyl)-2-aza-bicyclo[3.3.1]non-5-yl]-phenyl}-methanesulfonamide;
N-{3-[2-(3-Phenyl-propyl)-2-aza-bicyclo[3.3.1]non-5-yl]-phenyl}-methanesulfonamide;
N-{3-[2-(4-Methoxy-benzyl)-2-aza-bicyclo[3.3.1]non-5-yl]-phenyl}-methanesulfonamide;
N-{3-[2-(3-Cyclohexyl-propyl)-2-aza-bicyclo[3.3.1]non-5-yl]-phenyl}-methanesulfonamide;
N-(3-{2-[3-(1-Hydroxy-cyclopentyl)-propyl]-2-aza-bicyclo[3.3.1]non-5-yl}-phenyl)-methanesulfonamide;
N-{3-[2-(1H-Indol-3-ylmethyl)-2-aza-bicyclo[3.3.1]non-5-yl]-phenyl}-methanesulfonamide;
N-[3-(2-Benzofuran-2-ylmethyl-2-aza-bicyclo[3.3.1]non-5-yl)-phenyl]-methanesulfonamide;
N-[3-(2-Indan-2-ylmethyl-2-aza-bicyclo[3.3.1]non-5-yl)-phenyl]-methanesulfonamide;
N-[3-(2-Naphthalen-2-ylmethyl-2-aza-bicyclo[3.3.1]non-5-yl)-phenyl]-methanesulfonamide;
N-[3-(2-Naphthalen-1-ylmethyl-2-aza-bicyclo[3.3.1]non-5-yl)-phenyl]-methanesulfonamide;
N-(3-{2-[3-(1-Hydroxy-cyclohexyl)-propyl]-2-aza-bicyclo[3.3.1]non-5-yl}-phenyl)-methanesulfonamide;
N-(3-{2-[3-(1-Hydroxymethyl-cyclopentyl)-propyl]-2-aza-bicyclo[3.3.1]non-5-yl}-phenyl)-methanesulfonamide;
N-[3-(2-Quinolin-4-ylmethyl-2-aza-bicyclo[3.3.1]non-5-yl)-phenyl]-methanesulfonamide;
N-[3-(2-Quinolin-3-ylmethyl-2-aza-bicyclo[3.3.1]non-5-yl)-phenyl]-methanesulfonamide;
N-{3-[2-(4-Chloro-2-fluoro-benzyl)-2-aza-bicyclo[3.3.1]non-5-yl]-phenyl}-methanesulfonamide;
N-{3-[2-(1-Methyl-1H-indol-3-ylmethyl)-2-aza-bicyclo[3.3.1]non-5-yl]-phenyl}-methanesulfonamide;
N-{3-[2-(1,2,3,4-Tetrahydro-naphthalen-2-ylmethyl)-2-aza-bicyclo[3.3.1]non-5-yl]-phenyl}-methanesulfonamide;
N-{3-[2-(3-Phenyl-cyclobutylmethyl)-2-aza-bicyclo[3.3.1]non-5-yl]-phenyl}-methanesulfonamide;
N-{3-[2-(2-Hydroxy-indan-2-ylmethyl)-2-aza-bicyclo[3.3.1]non-5-yl]-phenyl}-methanesulfonamide;
N-{3-[2-(2-Phenethyloxy-ethyl)-2-aza-bicyclo[3.3.1]non-5-yl]-phenyl}-methanesulfonamide;
N-{3-[2-(4-Hydroxy-naphthalen-1-ylmethyl)-2-aza-bicyclo[3.3.1]non-5-yl]-phenyl}-methanesulfonamide;
N-{3-[2-(3-Indan-2-yl-propyl)-2-aza-bicyclo[3.3.1]non-5-yl]-phenyl}-methanesulfonamide;

N-{3-[2-(4-Pyrrolidin-1-yl-benzyl)-2-aza-bicyclo[3.3.1]non-5-yl]-phenyl}-methan esulfonamide;
N-{3-[2-(2-Hydroxy-1,2,3,4-tetrahydro-naphthalen-2-ylmethyl)-2-aza-bicyclo[3.3.1]non-5-yl]-phenyl}-methanesulfonamide;
N-{3-[2-(1-Hydroxy-3-phenyl-cyclobutylmethyl)-2-aza-bicyclo[3.3.1]non-5-yl]-phenyl}-methanesulfonamide;
N-{3-[2-(3-Methyl-benzo[b]thiophen-2-ylmethyl)-2-aza-bicyclo[3.3.1]non-5-yl]-phenyl}-methanesulfonamide;
N-(3-{2-[2-(4-Chloro-phenyl)-2-cyano-ethyl]-2-aza-bicyclo[3.3.1]non-5-yl}-phenyl)-methanesulfonamide;
N-[3-(2-Biphenyl-4-ylmethyl-2-aza-bicyclo[3.3.1]non-5-yl)-phenyl]-methanesulfonamide;
N-{3-[2-(3-Trifluoromethoxy-benzyl)-2-aza-bicyclo[3.3.1]non-5-yl]-phenyl}-methan esulfonamide;
N-(3-{2-[3-(2-Hydroxy-indan-2-yl)-propyl]-2-aza-bicyclo[3.3.1] non-5-yl}-phenyl)-methanesulfonamide;
N-{3-[2-(9H-Fluoren-2-ylmethyl)-2-aza-bicyclo[3.3.1]non-5-yl]-phenyl}-methanesu lfonamide;
N-{3-[2-(3-Phenoxy-benzyl)-2-aza-bicyclo[3.3.1]non-5-yl]-phenyl}-methanesulfonamide;
N-{3-[2-(4-Dimethylamino-naphthalen-1-ylmethyl)-2-aza-bicyclo[3.3.1]non-5-yl]-phe nyl}-methanesulfonamide;
2-Methoxy-ethanesulfonic acid [3-(2-ethyl-2-aza-bicyclo[3.3.1]non-5-yl)-phenyl]-amide;
2-Methoxy-ethanesulfonic acid [3-(2-cyclopropylmethyl-2-aza-bicyclo[3.3.1]non-5-yl)-phenyl]-amide;
2-Methoxy-ethanesulfonic acid [3-(2-isobutyl-2-aza-bicyclo[3.3.1]non-5-yl)-phenyl]-amide;
2-Methoxy-ethanesulfonic acid {3-[2-(3-methyl-butyl)-2-aza-bicyclo[3.3.1]non-5-yl]-phenyl}-amide;
2-Methoxy-ethanesulfonic acid [3-(2-pentyl-2-aza-bicyclo[3.3.1]non-5-yl)-phenyl]-amide;
2-Methoxy-ethanesulfonic acid {3-[2-(1H-pyrrol-2-ylmethyl)-2-aza-bicyclo[3.3.1]non-5-yl]-phenyl}-amide;
2-Methoxy-ethanesulfonic acid {3-[2-(1H-imidazol-2-ylmethyl)-2-aza-bicyclo[3.3.1]non-5-yl]-phenyl}-amide;
2-Methoxy-ethanesulfonic acid {3-[2-(1-hydroxy-cyclobutylmethyl)-2-aza-bicyclo[3.3.1]non-5-yl]-phenyl}-amide;
2-Methoxy-ethanesulfonic acid [3-(2-hexyl-2-aza-bicyclo[3.3.1]non-5-yl)-phenyl]-amide;
2-Methoxy-ethanesulfonic acid {3-[2-(2-ethyl-butyl)-2-aza-bicyclo[3.3.1]non-5-yl]-phenyl}-amide;
2-Methoxy-ethanesulfonic acid {3-[2-(1-methyl-1H-pyrrol-2-ylmethyl)-2-aza-bicyclo[3.3.1]non-5-yl]-phenyl}-amide;
2-Methoxy-ethanesulfonic acid [3-(2-thiophen-3-ylmethyl-2-aza-bicyclo[3.3.1]non-5-yl)-phenyl]-amide;
2-Methoxy-ethanesulfonic acid [3-(2-thiazol-2-ylmethyl-2-aza-bicyclo[3.3.1]non-5-yl)-phenyl]-amide;
2-Methoxy-ethanesulfonic acid {3-[2-(1-hydroxymethyl-cyclobutylmethyl)-2-aza-bicyclo[3.3.1]non-5-yl]-phenyl}-amide;
2-Methoxy-ethanesulfonic acid [3-(2-heptyl-2-aza-bicyclo[3.3.1]non-5-yl)-phenyl]-amide;
2-Methoxy-ethanesulfonic acid [3-(2-phenethyl-2-aza-bicyclo[3.3.1]non-5-yl)-phenyl]-amide;
2-Methoxy-ethanesulfonic acid (3-[2-(3-cyclopentyl-propyl)-2-aza-bicyclo[3.3.1]non-5-yl]-phenyl}-amide;
2-Methoxy-ethanesulfonic acid {3-[2-(2-ethyl-hexyl)-2-aza-bicyclo[3.3.1]non-5-yl]-phenyl}-amide;
2-Methoxy-ethanesulfonic acid [3-(2-octyl-2-aza-bicyclo[3.3.1]non-5-yl)-phenyl]-amide;
2-Methoxy-ethanesulfonic acid {3-[2-(3-phenyl-prop-2-ynyl)-2-aza-bicyclo[3.3.1]non-5-yl]-phenyl}-amide;
2-Methoxy-ethanesulfonic acid {3-[2-(3-phenyl-propyl)-2-aza-bicyclo[3.3.1]non-5-yl]-phenyl}-amide;
2-Methoxy-ethanesulfonic acid {3-[2-(4-methoxy-benzyl)-2-aza-bicyclo[3.3.1]non-5-yl]-phenyl}-amide;
2-Methoxy-ethanesulfonic acid {3-[2-(3-cyclohexyl-propyl]-2-aza-bicyclo[3.3.1]non-5-yl]-phenyl}-amide;
2-Methoxy-ethanesulfonic acid (3-{2-[3-(1-hydroxy-cyclopentyl)-propyl]-2-aza-bicyclo[3.3.1]non-5-yl}-phenyl)-amide;
2-Methoxy-ethanesulfonic acid {3-[2-(1H-indol-3-ylmethyl)-2-aza-bicyclo[3.3.1]non-5-yl]-phenyl}-amide;
2-Methoxy-ethanesulfonic acid [3-(2-benzofuran-2-ylmethyl-2-aza-bicyclo[3.3.1]non-5-yl)-phenyl]-amide;
2-Methoxy-ethanesulfonic acid [3-(2-indan-2-ylmethyl-2-aza-bicyclo[3.3.1]non-5-yl)-phenyl ]-amide;
2-Methoxy-ethanesulfonic acid [3-(2-naphthalen-2-ylmethyl-2-aza-bicyclo[3.3.1]non-5-yl)-phenyl]-amide;
2-Methoxy-ethanesulfonic acid [3-(2-naphthalen-1-ylmethyl-2-aza-bicyclo[3.3.1]non-5-yl)-phenyl]-amide;
2-Methoxy-ethanesulfonic acid (3-{2-[3-(1-hydroxy-cyclohexyl)-propyl]-2-aza-bicyclo[3.3.1]non-5-yl}-phenyl)-amide;
2-Methoxy-ethanesulfonic acid (3-{2-[3-(1-hydroxymethyl-cyclopentyl)-propyl]-2-aza-bicyclo[3.3.1]non-5-yl}-phenyl)-amide;
2-Methoxy-ethanesulfonic acid [3-(2-quinolin-4-ylmethyl-2-aza-bicyclo[3.3.1]non-5-yl)-phenyl]-amide;
2-Methoxy-ethanesulfonic acid [3-(2-quinolin-3-ylmethyl-2-aza-bicyclo[3.3.1]non-5-yl)-phenyl]-amide;
2-Methoxy-ethanesulfonic acid {3-[2-(4-chloro-2-fluoro-benzyl)-2-aza-bicyclo[3.3.1]non-5-yl]-phenyl}-amide;
2-Methoxy-ethanesulfonic acid {3-[2-(1-methyl-1H-indol-3-ylmethyl)-2-aza-bicyclo[3.3.1]non-5-yl]-phenyl}-amide;
2-Methoxy-ethanesulfonic acid {3-[2-(1,2,3,4-tetrahydro-naphthalen-2-yl methyl)-2-aza-bicyclo[3.3.1]non-5-yl]-phenyl}-amide;
2-Methoxy-ethanesulfonic acid {3-[2-(3-phenyl-cyclobutylmethyl)-2-aza-bicyclo[3.3.1]non-5-yl]-phenyl}-amide;
2-Methoxy-ethanesulfonic acid {3-[2-(2-hydroxy-indan-2-ylmethyl)-2-aza-bicyclo[3.3.1]non-5-yl]-phenyl}-amide;
2-Methoxy-ethanesulfonic acid {3-[2-(2-phenethyloxy-ethyl)-2-aza-bicyclo[3.3.1]non-5-yl]-phenyl}-amide;
2-Methoxy-ethanesulfonic acid {3-[2-(4-hydroxy-naphthalen-1-ylmethyl)-2-aza-bicyclo[3.3.1]non-5-yl]-phenyl}-amide;
2-Methoxy-ethanesulfonic acid {3-[2-(3-indan-2-yl-propyl)-2-aza-bicyclo[3.3.1]non-5-yl]-phenyl}-amide;
2-Methoxy-ethanesulfonic acid {3-[2-(4-pyrrolidin-1-yl-benzyl)-2-aza-bicyclo[3.3.1]non-5-yl]-phenyl}-amide;
2-Methoxy-ethanesulfonic acid {3-[2-(2-hydroxy-1,2,3,4-tetrahydro-naphthalen-2-ylmethyl)-2-aza-bicyclo[3.3.1]non-5-yl]-phenyl}-amide;
2-Methoxy-ethanesulfonic acid {3-[2-(1-hydroxy-3-phenyl-cyclobutylmethyl)-2-aza-bicyclo[3.3.1]non-5-yl]-phenyl}-amide;
2-Methoxy-ethanesulfonic acid {3-[2-(3-methyl-benzo[b]thiophen-2-ylmethyl)-2-aza-bicyclo[3.3.1]non-5-yl]-phenyl}-amide;
2-Methoxy-ethanesulfonic acid (3-{2-[2-(4-chloro-phenyl)-2-cyano-ethyl]-2-aza-bicyclo[3.3.1]non-5-yl}-phenyl)-amide;
2-Methoxy-ethanesulfonic acid [3-(2-biphenyl-4-ylmethyl-2-aza-bicyclo[3.3.1]non-5-yl)-phenyl]-amide;
2-Methoxy-ethanesulfonic acid {3-[2-(3-trifluoromethoxy-benzyl)-2-aza-bicyclo[3.3.1]non-5-yl]-phenyl}-amide;
2-Methoxy-ethanesulfonic acid (3-{2-[3-(2-hydroxy-indan-2-yl)-propyl]-2-aza-bicyclo[3.3.1]non-5-yl}-phenyl)-amide;

2-Methoxy-ethanesulfonic acid {3-[2-(9H-fluoren-2-ylm-ethyl)-2-aza-bicyclo[3.3.1]non-5-yl]-phenyl}-amide;
2-Methoxy-ethanesulfonic acid {3-[2-(3-phenoxy-benzyl)-2-aza-bicyclo[3.3.1]non-5-yl]-phenyl}-amide and
2-Methoxy-ethanesulfonic acid {3-[2-(4-dimethylamino-naphthalen-1-ylmethyl)-2-aza-bicyclo[3.3.1]non-5-yl]-phenyl}-amide and pharmaceutically acceptable salts of said compounds.

The compounds of the present invention may be used to bind to and modulate (i.e., inhibit, partially inhibit, activate or partially activate) an opioid receptor or receptors in a mammal, including a human. The present compounds exhibit pharmacological activity consistent with such binding. Compounds according to the present invention may also be used as reference materials, reference standards, including calibration standards and as synthetic intermediates.

The subject invention is also directed to pharmaceutical compositions comprising an effective amount of one or more compounds according to the invention as otherwise described herein, optionally in combination with a pharmaceutically acceptable additive, carrier or excipient.

The subject invention also provides a pharmaceutical composition for treating in a mammal, including a human, in need thereof a disease state, disorder or condition mediated by an opioid receptor or receptors which composition comprises an amount of a compound according to formula I or a pharmaceutically acceptable salt thereof effective in modulating an opioid receptor or receptors and a pharmaceutically acceptable carrier.

The subject invention also provides a pharmaceutical composition for treating in a mammal, including a human, in need thereof a disorder or condition mediated by an opioid receptor or receptors which composition comprises an amount of a compound according to formula I or a pharmaceutically acceptable salt thereof effective in treating said disorder or condition and a pharmaceutically acceptable carrier.

The subject invention also provides a pharmaceutical composition for treating in a mammal, including a human, in need thereof a disorder or condition selected from irritable bowel syndrome; constipation; nausea; vomiting; pruritic dermatoses, for example allergic dermatitis or contact dermatitis; psoriasis; eczema; an insect bite; an eating disorder, for example anorexia, bulimia, or obesity; depression, anxiety, schizophrenia; drug addiction, for example alcohol addiction, amphetamine addiction, cocaine addiction or addiction to an opioid, for example morphine, opium, or heroin; an opioid overdose; a sexual dysfunction, for example erectile dysfunction or impotence; stroke; head trauma; traumatic brain injury; spinal damage; Parkinson's disease; Alzheimer's disease, age-related cognitive decline; and Attention Deficit and Hyperactivity Disorder; which composition comprises an amount of a compound of formula I or a pharmaceutically acceptable salt thereof effective in modulating an opioid receptor or receptors and a pharmaceutically acceptable carrier.

The subject invention also provides a pharmaceutical composition for treating in a mammal, including a human, in need thereof, a disorder or condition selected from irritable bowel syndrome; constipation; nausea; vomiting; pruritic dermatoses, for example allergic dermatitis or contact dermatitis; psoriasis; eczema; an insect bite; an eating disorder, for example anorexia, bulimia, or obesity; depression, anxiety, schizophrenia; drug addiction, for example alcohol addiction, amphetamine addiction, cocaine addiction or addiction to an opioid, for example morphine, opium, or heroin; an opioid overdose; a sexual dysfunction, for example erectile dysfunction or impotence; stroke; head trauma; traumatic brain injury; spinal damage; Parkinson's disease; Alzheimer's disease, age-related cognitive decline; and Attention Deficit and Hyperactivity Disorder; which composition comprises an amount of a compound of formula I or a pharmaceutically acceptable salt thereof effective in treating said disorder or condition and a pharmaceutically acceptable carrier.

Another aspect of the subject invention is directed to treating in a mammal, including a human, in need thereof, a disorder or condition mediated by an opioid receptor or receptors which method comprises administering to said mammal an amount of a compound according to formula I, or a pharmaceutically acceptable salt thereof, effective in modulating an opioid receptor or receptors.

The subject invention also provides a method for treating in a mammal, including a human, in need thereof, a disease state, disorder or condition selected from irritable bowel syndrome; constipation; nausea; vomiting; pruritic dermatoses, for example allergic dermatitis or contact dermatitis; psoriasis; eczema; an insect bite; an eating disorder, for example anorexia, bulimia, and obesity; depression, anxiety, schizophrenia; drug addiction, for example alcohol addiction, amphetamine addiction, cocaine addiction or addiction to an opioid, for example morphine, opium, or heroin; an opioid overdose; a sexual dysfunction, for example erectile dysfunction or impotence; stroke; head trauma; traumatic brain injury; spinal damage; Parkinson's disease; Alzheimer's disease, age-related cognitive decline; and Attention Deficit and Hyperactivity Disorder; which method comprises administering to said mammal an amount of a compound of formula I or a pharmaceutically acceptable salt thereof as described above effective to modulate an opioid receptor or receptors in said mammal.

The subject invention also provides a method for treating in a mammal, including a human, in need thereof, a disease state, disorder or condition selected from irritable bowel syndrome; constipation; nausea; vomiting; pruritic dermatoses, for example allergic dermatitis or contact dermatitis; psoriasis; eczema; an insect bite; an eating disorder, for example anorexia, bulimia, or obesity; depression, anxiety, schizophrenia; drug addiction, for example alcohol addiction, amphetamine addiction, cocaine addiction and addiction to an opioid, for example morphine, opium, or heroin; an opioid overdose; a sexual dysfunction, for example erectile dysfunction or impotence; stroke; head trauma; traumatic brain injury; spinal damage; Parkinson's disease; Alzheimer's disease, age-related cognitive decline; and Attention Deficit and Hyperactivity Disorder; which method comprises administering to said mammal an amount of a compound of formula I or a pharmaceutically acceptable salt thereof as described above effective in treating said disease state, disorder or condition in said mammal.

Thus, compounds of the present invention are useful because they possess pharmacological activity in animals, especially mammals, including humans. These compounds may also find use as standards in analytical assays or as intermediates in the synthesis of final compounds exhibiting pharmacological activity.

The subject invention also provides a method for treating in a mammal, including a human, in need thereof a disorder or condition mediated by an opioid receptor or. receptors which method comprises administering to said mammal an amount of a compound according to formula I or a pharmaceutically acceptable salt thereof effective in treating said disorder or condition.

In the therapeutic methods of the subject invention as described above, the disease state, disorder or condition that is being treated is preferably irritable bowel syndrome, drug addiction, depression, anxiety, schizophrenia, or an eating disorder.

Methods of synthesizing compounds according to the present invention and key intermediates which can be in such methods are additional aspects of the present invention. These methods are described in greater detail hereinbelow.

DETAILED DESCRIPTION OF THE INVENTION

The following terms shall be used to describe the subject invention.

The term "compound", as used herein, unless otherwise indicated, refers to any specific chemical compound disclosed herein. Within its use in context, the term generally refers to a single compound, but in certain instances may also refer to stereoisomers and/or optical isomers (including racemic mixtures), as well as specific enantiomers or enantiomerically enriched mixtures of disclosed compounds.

The term "effective" is used herein, unless otherwise indicated, to describe an amount of a compound which, in context, is used to produce or effect an intended result, whether that result relates to the treatment of a disease state, disorder or condition or alternatively, is used to produce another compound, agent or composition.

The terms "treatment", "treating", and the like, refers to reversing, alleviating, or inhibiting the progress of the disorder or condition to which such term applies, or one or more symptoms of such disorder or condition. As used herein, these terms also encompass, depending on the condition of the patient, preventing the onset of a disorder or condition, or of symptoms associated with a disorder or condition, including reducing the severity of a disorder or condition or symptoms associated therewith prior to affliction with said disorder or condition. Thus, "treatment", as used herein, can refer to administration of a compound of the invention to a subject that is not at the time of administration afflicted with the disorder or condition. "Treating" thus also encompasses preventing the recurrence of a disorder or condition or of symptoms associated therewith.

The term "addiction", as used herein, for example in "drug addiction" and "alcohol addiction", unless otherwise indicated, refers to a maladaptive use of a substance, which may be either with physiological dependence or without. The term "addiction" thus includes both substance abuse (e.g. alcohol, amphetamine, cocaine or an opioid, for example morphine, opium, or heroin abuse) and substance dependence (e.g. alcohol, amphetamine, cocaine or an opioid, for example morphine, opium, or heroin dependence). The maladaptive pattern of substance use may manifest itself in recurrent and significant adverse consequences related to the repeated use of the substance. The recurrent substance use may result in a failure to fulfill major role obligations at work, school, or home. The maladaptive use of a substance may involve continued use of the substance despite persistent or recurrent social or interpersonal problems caused or exacerbated by the effects of the substance (e.g., arguments with spouse, physical fights). The maladaptive pattern of substance use may involve clinically significant impairment or distress, for example manifested by tolerance for the substance, withdrawal symptoms, self-injurious behavior, unsuccessful efforts to cut down or control the substance use, and/or taking larger amounts of the substance and/or taking amounts of the substance over a longer period than was intended. Substances to which an addiction may be formed include, but are not limited to, the drugs recited above (including alcohol), as well as others, for example benzodiazepines such as Valium®.

The term "mammal", as used herein, and unless otherwise indicated, means any mammal. The term "mammal" includes, for example and without limitation, dogs, cats, and humans. The term "patient" or "subject" may be alternatively used to describe such a mammal, including a human, to whom treatment or use with the compounds or compositions according to the subject invention is provided. For treatment or use with/or of those disease states, conditions or disease states which are specific for a specific animal (especially, for example, a human subject or patient), the term patient or subject refers to that particular animal.

References herein to disease states, disorders and conditions "mediated by an opioid receptor or receptors" indicate disorders or conditions the treatment of which can be facilitated by modulating (i.e. inhibiting, partially inhibiting, activating, or partially activating) an opioid receptor or receptors. Examples of disorders and conditions the treatment of which is facilitated by modulation of an opioid receptor or receptors include, but are not limited to, irritable bowel syndrome, eating disorders, sexual dysfunction, depression, anxiety, schizophrenia and drug addictions, as well as the other specific disorders and conditions recited herein.

The term "alkyl", as used herein, unless otherwise indicated, includes saturated monovalent hydrocarbon radicals having straight, cyclic or branched moieties. Examples of alkyl groups include, but are not limited to, methyl, ethyl, propyl, isopropyl, sec-butyl and t-butyl. Within context, the use of the term "alkyl" may also subsume the use of or refer to alkylene groups, i.e., a hydrocarbon radical derived from alkyl groups which are diradicals, rather than monoradicals.

The term "cycloalkyl", as used herein, unless otherwise indicated, includes non-aromatic saturated cyclic alkyl moieties wherein alkyl is as defined above. Examples of cycloalkyl include, but are not limited to, cyclopropyl, cyclobutyl, cyclopentyl, cyclohexyl, and cycloheptyl.

The term "carbocyclic", as used herein, unless otherwise indicated, refers to a cyclic group in which all of the atoms of the ring are carbon atoms. Representative carbocyclic groups include cycloalkyl groups as described above. The term carbocyclic subsumes the term aryl within it.

The term "heterocyclic", as used herein, unless otherwise indicated, refers to a cyclic group in which at least one atom of the ring is a heteroatom (i.e., O, S or N). The term heterocyclic subsumes the term heteroaryl within it. Thus, a 5- to 7-membered heterocyclic group subsumes a 5- to 7-membered heteroaryl group within it.

The term "aryl", as used herein, unless otherwise indicated, includes an organic radical derived from an aromatic hydrocarbon by removal of one hydrogen, such as phenyl, naphthyl, indenyl, and fluorenyl.

The term "heteroaryl", as used herein, refers to aromatic groups containing one or more heteroatoms (O, S, or N), preferably from one to four heteroatoms. A multicyclic group containing one or more heteroatoms wherein at least one ring of the group is aromatic is a "heteroaryl" group. The heteroaryl groups of this invention can also include ring systems substituted with one or more oxo moieties. Examples of heteroaryl groups are pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyt, tetrahydroisoquinolyl, benzofuryl, furopyridinyl, pyrolopyrimidinyl, and azaindolyl. The foregoing groups, as derived from the compounds listed above, may be C-attached or N-attached where such is possible. For instance, a group derived from pyrrole may be pyrrol-1-yl (N-attached), pyrrol-2-yl or pyrrol-3-yl (C-attached). The terms referring to the groups also encompass all possible tautomers.

The term "phenyl-fused" or "heteroaryl-fused", as used herein, refers to a heterocyclic or carbocyclic group which forms a ring by attaching or bonding two atoms (carbon and/or heteroatoms) of the heterocyclic or carbocyclic group to two atoms of the phenyl or heteroaryl group.

The term "reductive amination", as used herein, refers to any process whereby the combination of an aldehyde or a ketone, or aldehyde or ketone equivalent, such as a bisulfite addition complex of an aldehyde, is combined with, in reference to the subject invention, a primary amine, secondary amine or ammonia, or ammonia source, such that the compounds condense to generate an intermediate imine or iminium ion that may be subjected to reduction by means of hydrogenation, such as mediated by a metal species such as palladium or platinum in many forms useful for reduction and a hydrogen source, such as hydrogen gas, or any precursor to hydrogen gas, including but not limited to formate derivatives or cyclohexadiene, or other hydride sources whereby hydride delivery from said source occurs by mechanisms commonly understood and employed. These include hydride reagents such as boron or aluminum hydride sources, for instance borohydrides, such as $[(X)_nBH_{4-n}]^-$ (n=0, 1, 2, 3) or aluminum hydrides such as $[(X)_nAlH_{4-n}]^-$ (n=0, 1, 2, 3) (wherein X may be any of the commonly cited ligands for transformations such a reductive amination including but not limited to acetoxy, trifluoroacetoxy, alkoxy, or lower alkyl for boron or alkoxy or lower alkyl for aluminum). Other hydrides may be equally suited to these transformations (for instance silanes or stannanes).

The term "reducing" or "reductive conditions", as used herein, refers to any process whereby dehydrohalogenation, hydrogenolysis, hydrogenation, or reduction of unsaturated bonds occurs as desired.

The term "leaving group", as used herein, refers to any group suitable in the conversion of a primary amine, secondary amine or ammonia or ammonia source that effectively departs in a bond-forming event from a carbon atom of interest, such as in an alkylation reaction. Suitable groups include halides (iodide, bromide or chloride), sulfonates (such methane sulfonate, trifluoromethanesulfonate or, aryl sulfonates such as tosyl or nosyl groups), epoxides or aziridines or any variation that is well known to those of skill in the art. In addition, the processes involving leabing groups may be employed in the formation of other C-X bonds where the nucleophile X is oxygen, sulfur, or carbon centered.

The term "carbonyl protecting group", as used herein, refers to any group that can withstand chemistry performed on other portions of the molecule without being substantially structurally compromised. Such groups must withstand reduction, reductive amination and alkylation chemistry as defined. These groups may include alkoxy groups such as dimethoxy, diethoxy, other $C_1$–$C_6$ dialkoxy, diphenoxy, or cyclic ketals such as cyclic dialkoxy groups such as dioxolanes, 1,3-dioxanes or catechols, among others.

Pharmaceutical salts of compounds according to the present invention are an important aspect. Pharmaceutical salts of compounds of formula I can be obtained by forming salts with any acidic or basic group present on a compound of formula I. Examples of pharmaceutically acceptable salts of the compounds of formula I are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, maleic acid, di-p-toluoyl tartaric acid, acetic acid, sulfuric acid, hydroiodic acid, mandelic acid, sodium, potassium, magnesium, calcium, and lithium. Mesylate and/or citrate salts may be particularly preferred in the subject invention.

As noted above, the compounds of formula I may have optical centers and therefore may occur in different enantiomeric and other stereoisomeric configurations. The invention includes all enantiomers, diastereomers, and other stereoisomers of such compounds of formula I, as well as racemic and other mixtures thereof.

The synthetic methods described below in the "Detailed Description" section and in Examples produce primarily compounds of formula I having the relative stereochemistry illustrated by compounds of formula I below:

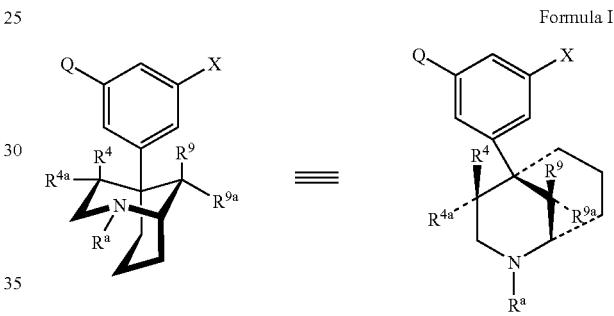

Formula I wherein $R^a$ is H or a

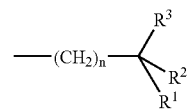

group.

Note that the two depictions of formula I above are equivalent (identical) chemical structures.

Isolation and purification of the products is accomplished by standard procedures which are known to a chemist of ordinary skill in the art. In addition, by following the disclosed chemistry more generically and/or by analogy, one of ordinary skill may readily provide all of the compounds according to the subject invention.

Scheme I–XI illustrate methods for the preparation of compounds having the basic structure of formula I, where Q=$NH_2$, $NHSO_2R^8$, $CONH_2$, $R^6$ and $R^9$=H or alkyl, and j, m, n, v, $R^1$, $R^2$ and $R^{15}$ are described as above. Other compounds according to the present invention may be readily synthesized by analogy following the specific methods described in detail herein and following well-known synthetic methods in the art.

As used herein, the expression "reaction inert solvent" refers to a solvent system in which the components do not interact with starting materials, reagents, or intermediates of products in a manner that adversely affects the yield of the desired product.

During any of the following synthetic sequences it may be necessary and/or desirable to protect sensitive or reactive groups on any of the molecules concerned. This may be achieved by means of conventional protecting groups, such as those described in T. W. Greene and P. G. M. Wuts, *Protective Groups in Organic Chemistry*, 3$^{rd}$ edition, John Wiley & Sons, 1999.

The stereochemistry of compounds of formula I synthesized according to the methods described above can be determined using standard spectroscopic methods. Isolation of the desired diastereomer of a compound of formula I from a diastereomeric mixture can be accomplished using standard separation methods know to those of ordinary skill in the art, for example crystallization or chromatographic methods.

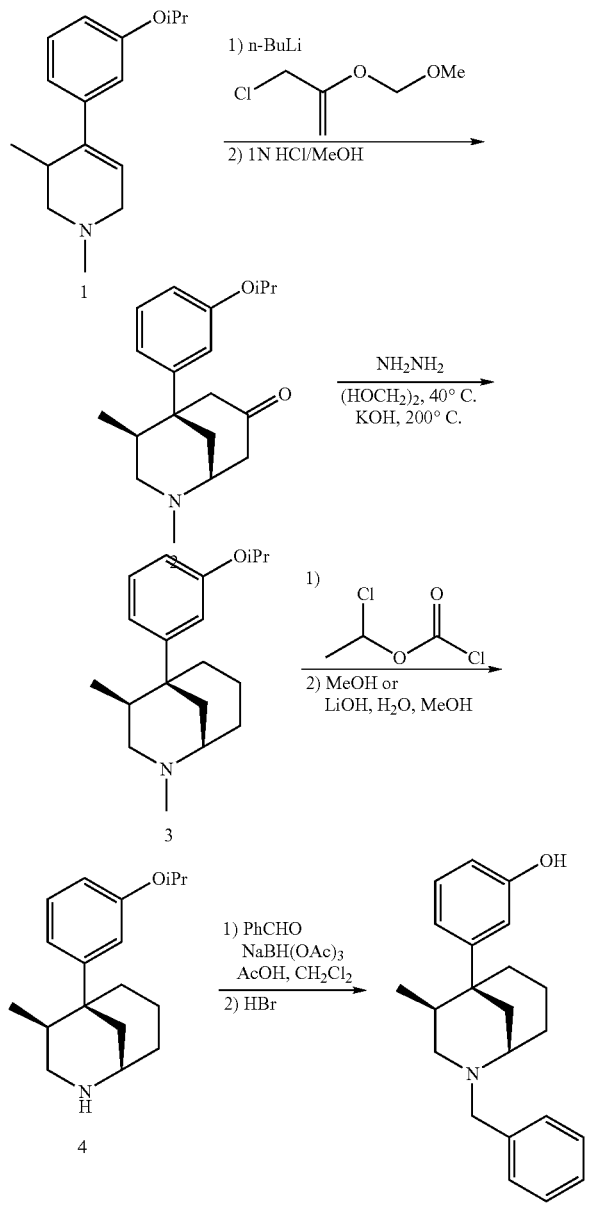

Referring to Scheme I above, certain compounds of formula I are known wherein Q=OH and R$^a$=H and described in the literature (see Werner, J. A.; Cerbone, L. R.; Frank, S. A.; Ward, J. A.; Labib, P.; Tharp-Taylor, R. W.; Ryan, C. W. *J. Org. Chem.* 1996, 61, 587–597 and WO2002060445A1). In these known preparations certain intermediates such as 1 as shown above in Scheme I have been described. These citations also include methods of the preparation of optically enriched and optically pure materials. These materials may be prepared as described therein or by adapted methods, as for instance in Scheme I whereby the ketone intermediate 2 is reduced under Wolff-Kishner conditions to give 3. Other methods of reducing ketones to methylene groups are equally applicable. Removal of the nitrogen radical by standard methods as known to those skilled in the art and described in the above articles affords intermediate 4. This intern may be converted to a nitrogen protected material suitable for further elaboration. Such materials may be accessed by known method such as alkylation, reductive alkylation or acylation and hydride reduction. Such methods are more fully described in Scheme IX, X and XI and in the Examples section. For the purposes of this description the conversion to a N-benzyl radical is convenient and sufficient. As shown in Scheme I such a conversion is shown from intermediate 4 which, after standard dealkylation of the phenyl alkyl ether, as by, for instance HBr in acetic acid at a temperature of room temperature to 100° C., provides 5. For the purposes of illustration this scheme demonstrates an approach to compounds of the invention where the R$^4$ radical, as described previously, is methyl.

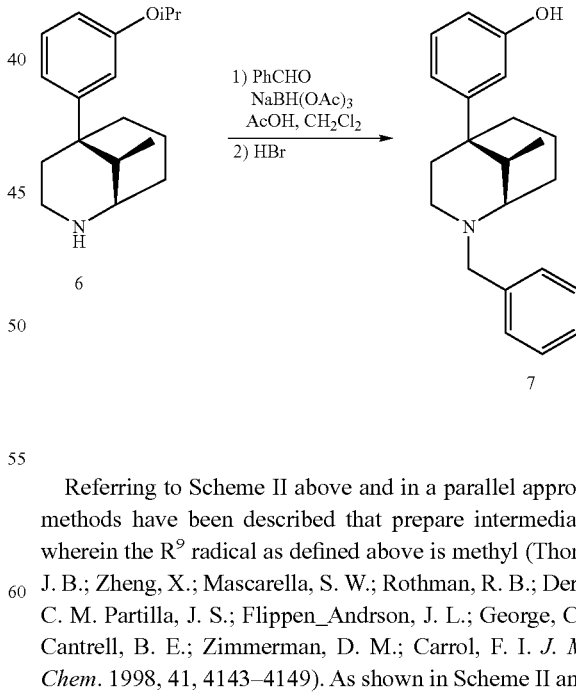

Referring to Scheme II above and in a parallel approach, methods have been described that prepare intermediate 6 wherein the R$^9$ radical as defined above is methyl (Thomas, J. B.; Zheng, X.; Mascarella, S. W.; Rothman, R. B.; Dersch, C. M. Partilla, J. S.; Flippen_Andrson, J. L.; George, C. F.; Cantrell, B. E.; Zimmerman, D. M.; Carrol, F. I. *J. Med. Chem.* 1998, 41, 4143–4149). As shown in Scheme II and as described for Scheme I, the conversion of this intermediate 6 provides N-protected intermediate 7, whereby, for the purposes of illustration, the N-radical is benzyl.

Scheme III

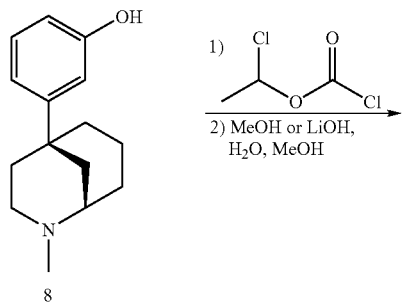

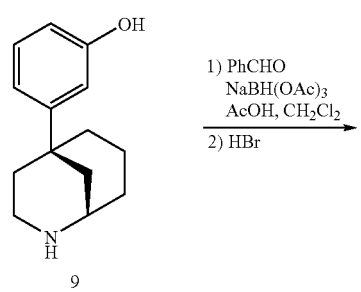

Scheme IV

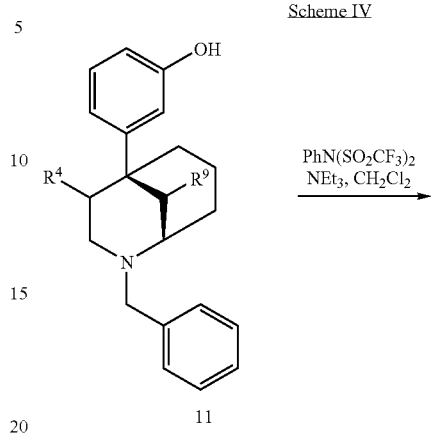

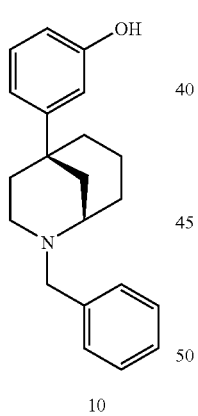

Referring to Scheme III above methods are shown for the preparation of compounds wherein both the $R^4$ and $R^9$ radicals are hydrogen and the N-protection is again a benzyl group introduced by methods described below in Scheme IX, X and XI. Methods have been described to prepare intermediate 8 (Bertha, C. M.; Mattson, M. V.; Flippen-Anderson, J. L.; Rothman, R. B.; Xu, H.; *J. Med. Chem.* 1994, 37, 3163–3170) and the conversion to a N-protected version compatible with subsequent chemical transformations is shown, via intermediate 9, to prepare intermediate 10.

Scheme IV shows a method of preparation of compounds of formula I wherein $Q=NH_2$ ($R^a=Bn$, $R^4$ or $R^9$ are as described above). These compounds may be derived from related precursors whereby $Q=OH$. Referring to Scheme IV, treatment of a compound of formula 11 (5, 7 and 10 being examples thereof) with $C_6H_5N(SO_2CF_3)_2$ in the presence of a suitable base, such as triethylamine in a solvent such as methylene chloride, will produce the trifluoromethanesulfonate (triflate) of formula 12. Treatment of a triflate of formula 12 with benzophenone imine with a suitable catalyst such as palladium (II) acetate, a suitable phosphine ligand such as BINAP, and a suitable base, such as sodium t-butoxide, in a suitable solvent such as toluene, at temperatures ranging from room temperature to about the reflux temperature, produces an intermediate imine, which is then treated with aqueous acid at temperatures ranging from room to reflux, preferably at 80–100° C., producing the aniline of formula 13.

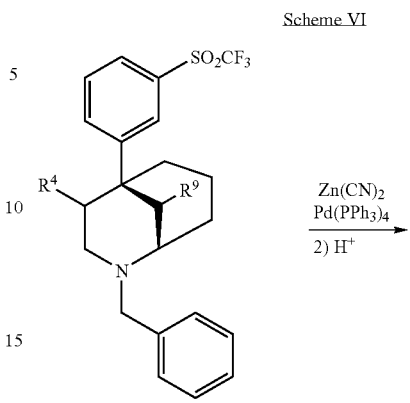

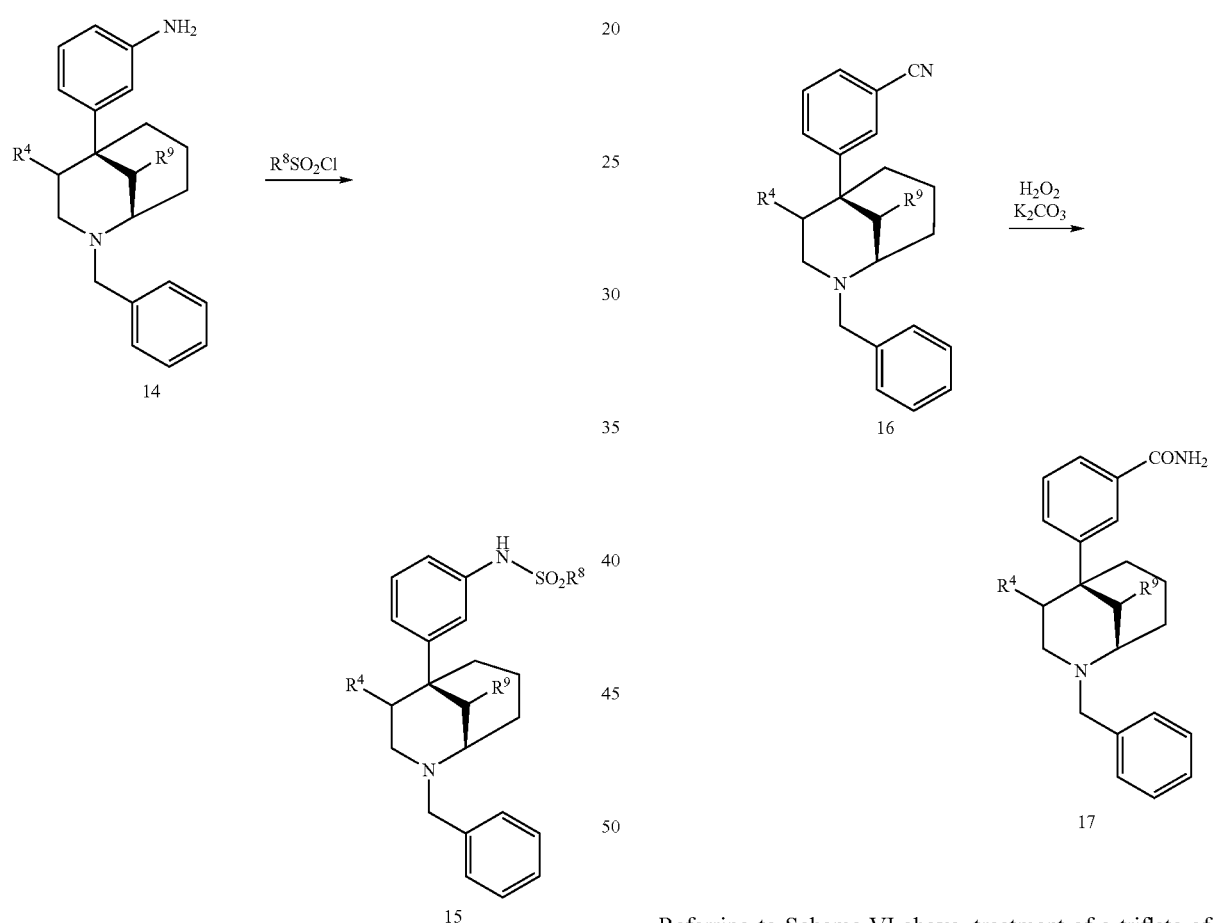

Referring to Scheme V, treatment of an aniline of formula 14 with an appropriately substituted sulfonyl chloride or anhydride such as methanesulfonyl chloride or 2-methoxyethanesulfonyl chloride, in the presence of a suitable base, such as pyridine, in a solvent such as methylene chloride, at temperatures ranging from 0° C. to room temperature, preferably at about room temperature, produces the desired sulfonamide of formula 15.

Referring to Scheme VI above, treatment of a triflate of formula 12 with zinc cyanide, in the presence of a suitable catalyst, such as tetrakistriphenylphosphine palladium (0), in solvents such as dimethylformamide, at temperatures ranging from room temperature to about reflux temperature, preferably at about 85° C., produces the corresponding nitrile of formula 16. Conversion of a nitrile of formula 16 by the action of for instance dilute hydrogen peroxide, in the presence of a suitable alkali metal base, such as potassium carbonate, in solvents such as dimethylformamide or dimethylsulfoxide, at temperatures ranging from 0° C. to about room temperature, preferably at about room temperature, produces the corresponding amide of formula 17.

Scheme VII

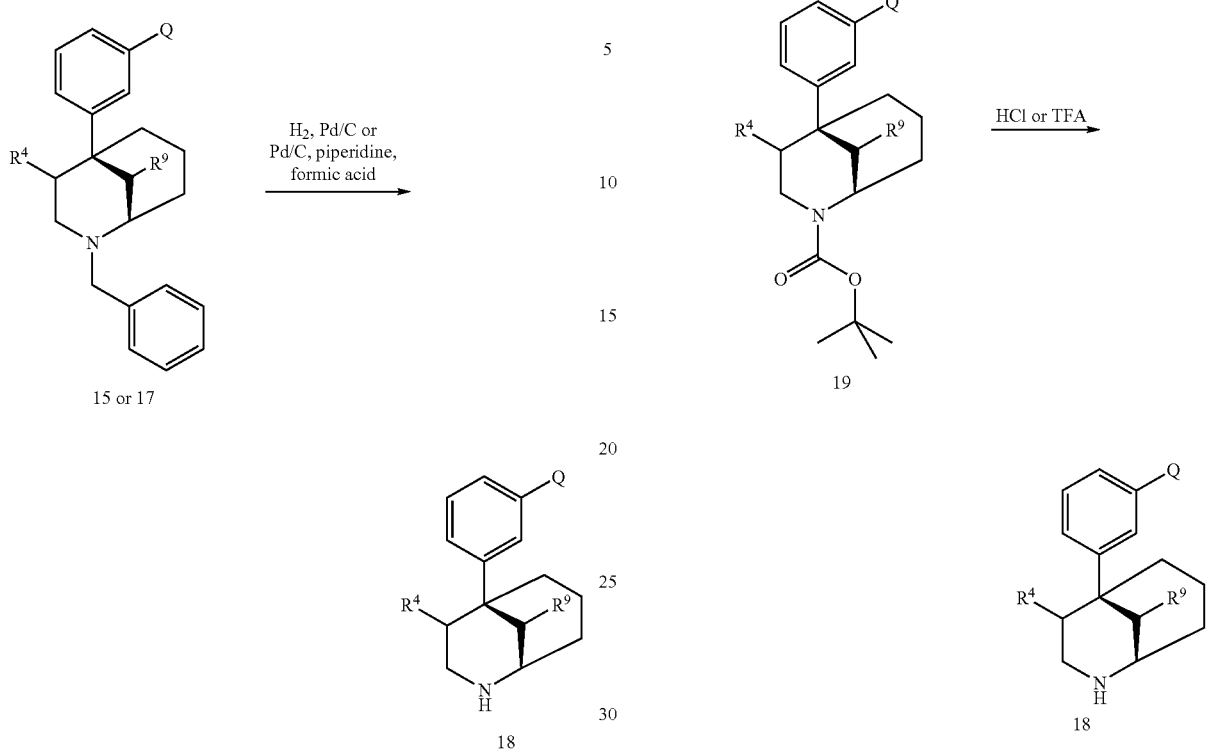

Referring to Scheme VII above, compounds of formula I ($R^a$=H) can be prepared by the reduction or hydrogenolysis of compounds of formula 15 or 17 with hydrogen gas (at pressures ranging from atmospheric to 50 psi) in the presence of a suitable catalyst such as palladium on carbon, in alcoholic solvents such as methanol, at temperatures ranging from room temperature to reflux, preferably at about 60° C. Alternatively, compounds of formula I ($R^a$=H) can be prepared by treatment of compounds of formula 15 or 17 with ammonium salts of formic acid, such as ammonium formate, or more preferably, that formed by contacting piperidine and formic acid, in the presence of a suitable catalyst, such as palladium on carbon, in alcoholic solvents, such as methanol or ethanol, at temperatures ranging from room temperature to about the reflux temperature, preferably at about reflux temperature. These methods are useful for the conversion of any compound wherein Q or X as described previously is stable to the conditions as described here as may be determined by one skilled in the art.

Scheme VIII

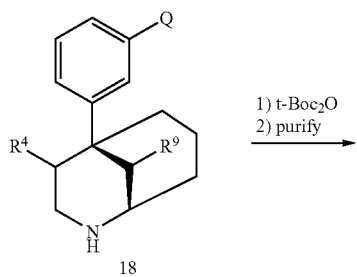

As shown above in Scheme VII, compounds of formula I ($R^a$=H, 18) can be converted to derivatives that allow for ready purification and isolation. It is often sufficient to remove protective $R^a$ groups as described in Scheme VII and purify these products by standard methods such as crystallization or chromatography. On occasion it is convenient to prepare protected intermediates that are readily purified by standard methods such as crystallization or chromatography, and which are then readily converted back to compounds where $R^a$=H. In such an approach, the t-butyloxy-carbonyl protecting group may be introduced, or any other convenient protecting group, by standard methods, such as by contacting di-t-butyldicarbonate with compounds of formula I where $R^a$ is H, 18. This may be done in any solvent that allows the conversion to occur, such as a chlorinated solvent like dichloromethane or dichloroethane, an ethereal solvent such as THF or dioxane or water. Base may or may not me necessary, for instance alkali carbonates or bicarbonates or the like. An effective method calls for adding di-t-butyidicarbonate to compounds of formula I where $R^a$ is H (18) in dichloromethane or THF in the presence of aqueous sodium bicarbonate or carbonate solutions. The product materials 19 are then readily separated from byproducts of the transfer hydrogenolysis reaction in Scheme VII, if still present, for instance t-piperidine-1-carboxylic acid tert-butyl ester, by chromatographic methods. Removal of this group is readily accomplished by any of the methods known to those in the art, such as in the conversion to the HCl or trifluoroacetate salts of compounds of formula I ($R^a$=H, 18) by expose of 19 to the acid in a non-aqueous medium.

Scheme IX

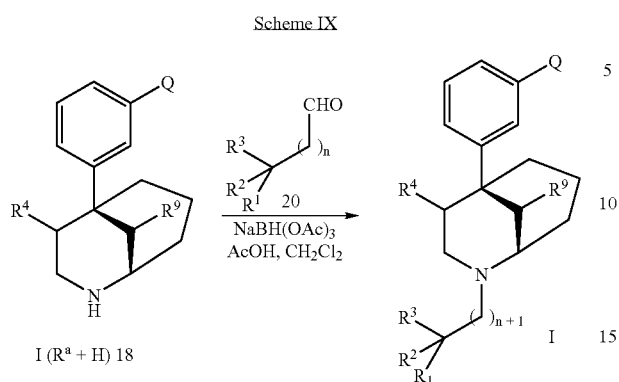

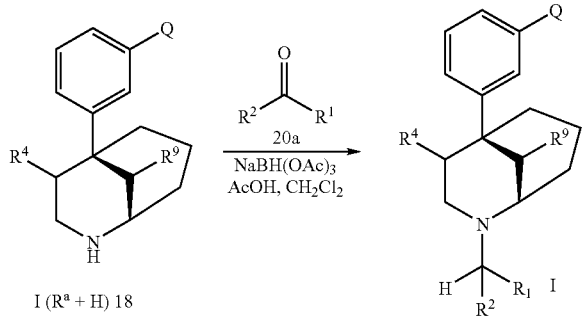

Referring to Scheme IX, treatment of a compound of formula I ($R^a$=H, 18) with an appropriately substituted aldehyde of formula 20 (or the corresponding alkali metal bisulfite addition compound of said aldehyde) and a reducing agent such as sodium triacetoxyborohydride, in the presence of acetic acid, in solvents such as chlorinated solvents, such as dichloromethane or dichloroethane or an alcohol, such as methanol, or an ethereal solvent such as THF, or any combination of these solvents, at temperatures ranging from 0° C. to about room temperature, preferably at about room temperature, produce the corresponding compounds of formula I. Precursors to this step can be prepared using methods that are known to one of ordinary skill in the art. Equally useful in this step is the use of ketones of formula 20a such that compounds wherein n=0 may be prepared.

Scheme X

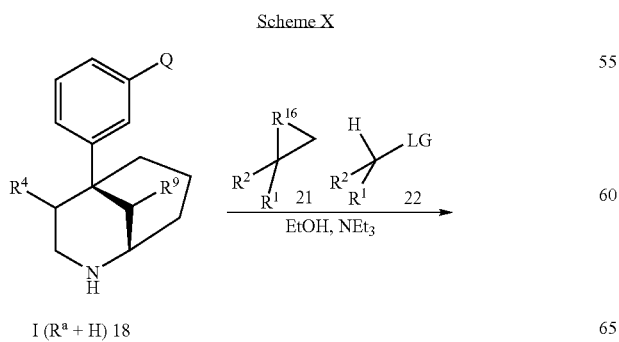

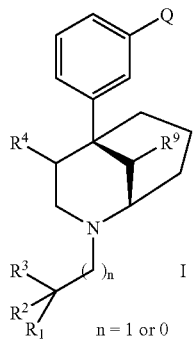

Referring to Scheme X above, compounds of formula I can be prepared by treatment of a compound of formula I ($R^a$=H, 18) with a reagent of formula 21 wherein $R^{16}$ is oxygen or —NH or —NSO$_2$R or —NCOOR, or a compound of formula 22 wherein LG (leaving group) is a suitable sulfonate, such as methansulfonate, trifluoromethanesulfonate or arylsulfonate, or a halide, such as chloride, bromide or iodide. This reaction should be carried out in the presence of a suitable base such as a tertiary amine, for instance triethylamine, in alcoholic solvents such as ethanol or isopropanol at temperatures ranging from room temperature to about the reflux temperature, preferably at about the reflux temperature to produce the desired compound of formula I.

Scheme XI

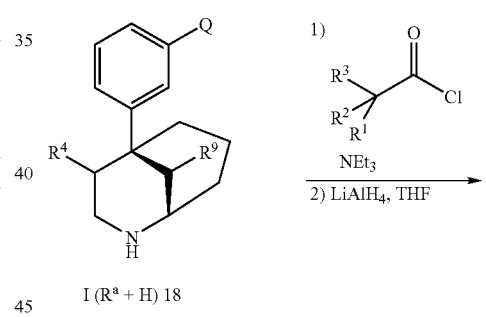

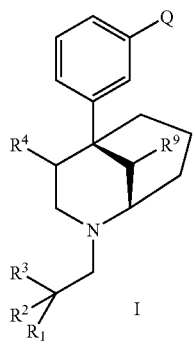

Alternatively, referring to Scheme XI compounds of formula I can also be prepared by treatment of a compound of formula I ($R^a$=H, 18) with an appropriately substituted acid chloride of formula 23. The reaction should be carried out in the presence of a suitable base such as hydroxide ion, Et$_3$N or pyridine, in solvents such as water, tetrahydrofuran or methylene chloride, at temperature ranging from 0° C. to room temperature, preferably at about room temperature. Any of the suitable methods for preparing amides known to those skilled in the art are appropriate for use in this transformation. The amide products from this reaction (not depicted) are then reduced with a suitable reducing agent, such as lithium aluminum hydride Dibal-H or borane in solvents such as ethyl ether or tetrahydrofuran, at temperatures ranging from room temperature to about the reflux temperature, preferably at about the reflux temperature, which produce the desired products of formula I. Any of the suitable methods for reducing amides known to those skilled in the art that will not affect other functionalities present in the target compound are appropriate for use in this transformation. In reference to Schemes X and XI reagents 21, 22 and 23 can be prepared using methods that are readily known to one of ordinary skill in the art.

The subject invention also includes isotopically-labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3H$, $^{11}C$, $^{14}C$, $^{18}F$, $^{123}I$ and $^{125}I$. Compounds of the subject invention and pharmaceutically acceptable salts of said compounds that contain the aforementioned isotopes and/or other isotopes of other atoms are within the scope of this invention. Isotopically labeled compounds of the subject invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of formula I of this invention can generally be prepared by carrying out the procedures disclosed in the Schemes and/or in the Examples above, by substituting a readily available isotopically labeled reagent for a non-isotopically labeled reagent.

Accordingly, the subject invention also provides a compound of formula I wherein one or more atoms thereof have an atomic mass or mass number different from the atomic mass or mass number usually found in nature, or a pharmaceutically acceptable salt of such compound. The subject invention also provides a method for obtaining an image of opioid receptors in a mammalian, including a human, subject which method comprises administering to said subject an amount of an isotopically-labeled compound of formula I, or pharmaceutically acceptable salt thereof, effective in imaging opioid receptors in said subject.

Pharmaceutically acceptable salts of a compound of formulas I or II can be prepared in a conventional manner by treating a solution or suspension of the corresponding free base or acid with a pharmaceutically acceptable acid or base. Conventional concentration or crystallization techniques can be employed to isolate the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluene-sulfonic, and related acids. Illustrative bases are sodium, potassium, and calcium.

A compound of this invention may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining a compound of formula I or a pharmaceutically acceptable salt thereof can then be readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing a compound of this invention or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

A compound of formula I or a pharmaceutically acceptable salt thereof can be administered orally, transdermally (e.g., through the use of a patch), parenterally (e.g. intravenously), rectally, topically, or by inhalation. In general, the daily dosage for treating a disorder or condition as described herein using a compound of formula I will be about from about 0.01 to about 100 mg per kg, preferably from about 0.1 to about 10 mg per kg, of the body weight of the animal to be treated. As an example, a compound of the formula I, or a pharmaceutically acceptable salt thereof, can be administered for treatment to an adult human of average weight (about 70 kg) in a dose ranging from about 0.5 mg up to about 10 g per day, preferably from about 1 mg to about 1 g per day, in single or divided (i.e., multiple) portions. Variations based on the aforementioned dosage ranges may be made by a physician of ordinary skill taking into account known considerations such as the weight, age, and condition of the animal being treated, the severity of the affliction, and the particular route of administration chosen.

Biological Activity

Compounds of formula I of the subject invention have been found to display activity in opioid receptor binding assays selective for the mu, kappa and delta opioid receptors. Assays for mu, kappa and delta opioid receptor binding can be performed according to the following procedures.

Affinity of a compound for the delta opioid receptor can be assessed using binding of the delta opioid receptor ligand [$^3$H]-naltrindole to NG108-15 neuroblastoma-glioma cells according to modification of the protocol described in Law et al. (Law, P. Y., Koehler, J. E. and Loh, H. H., "Comparison of Opioid Inhibition of Adenylate Cyclase Activity in Neuroblastoma N18TG2 and Neuroblastoma X Glioma NG108-15 Hybrid Cell Lines", *Molecular Pharmacology*, 21: 483–491 (1982)). Law et al. is incorporated herein in its entirety by reference. Affinity of a compound for the kappa opioid receptor can be assessed using binding of [$^3$H]-bremazocine to kappa receptors as described in Robson, L. E., et al., "Opioid Binding Sites of the Kappa-type in Guinea-pig Cerebellum", *Neuroscience (Oxford)*, 12(2): 621–627 (1984). Robson et al. is incorporated herein it its entirey by reference. For assessment of a compound for mu opioid receptor activity, the mu receptor ligand [$^3$H]-DAMGO (Perkin Elmer Life Sciences, Boston, Mass.; specific activity 55 Ci/mmol, 1.5 nM) is used with rat forebrain tissue. Briefly, the binding is initiated with the addition of a crude membrane preparation of rat forebrain tissue to 96-well polypropylene plates containing the radioligand [$^3$H]-DAMGO and test compound, and are incubated for about 90 minutes at about 25° C. The assay is terminated by rapid filtration with 50 mM Tris HCl pH 7.4 onto Wallac Filtermat B and counted on a Betaplate reader (Wallac).

The data generated can be analyzed using IC$_{50}$ analysis software in Graphpad Prism. Ki values can be calculated using Graphpad Prism according to the following formula:

$Ki = IC_{50}/1 + [^3H \text{ ligand}]/K_D$ where IC$_{50}$ is the concentration at which 50% of the $^3$H ligand is displaced by the test compound and K$_D$ is the dissociation constant for the $^3$H ligand at the receptor site.

The Ki values of certain compounds of formula I of the Examples, as described, infra, in a mu opioid receptor binding assay to brain tissue such as that described above, were determined. All of the compounds tested in this manner were all found to have Ki values of about 800 nM or less for the mu opioid receptor.

The inhibition (%) of [$^3$H]-DAMGO binding by certain compounds of formula I of the Examples, as described, infra, in a mu opioid receptor binding assay to brain tissue such as that described above, were determined. Most of the compounds tested at 100 nM were found to inhibit [$^3$H]-DAMGO binding at the mu opioid receptor in a range of 10–100%.

Other assays which may be used for determining the binding of compounds according to the present invention to opioid receptors are well known in the art. These assays may be used to assess the ability of a compound to modulate (i.e., inhibit, partially inhibit, activate or partially activate) an opioid receptor or receptors by determining a compound's agonist or antagonist activity in the in vitro or in vivo assay. These assays include, for example, the GTP gamma S binding assay as described in Martin, et al., *J. Pharm. Exp. Ther.*, 301, 661–671 (2003) and Zaki, et al., *J. Pharm. Exp. Ther.*, 298, 1015–1020 (2002), as well as other binding assays, such as the isolated guinea pig ileum and receptor binding assay as disclosed, for example, by Takayama, et al., *J. Med. Chem.*, 45, 1949–1956 (2002) and the guinea pig brain binding assay as described by Wentland, et al., *J. Med. Chem.*, 46, 838–849 (2003). The use of mouse brain tissue to determine the functional activity of the compounds of interest is another binding assay which can be used for characterizing the modulation of the present compounds at opioid receptors, as disclosed by Martin, et al., Idem. Other binding assays include the tail-flick assay in mice or the radiant heat paw-withdrawal hyperalgesic testing in mice, as described by Hosohata, et al., *J. Pharm. Exp. Ther.*, 304, 683–688 (2003), among others. These assays or variations of these assays are well-known to those of ordinary skill in the art.

EXAMPLES

Preparation 1

3-(2-Benzyl-2-aza-bicyclo[3.3.1]non-5-yl)-phenol $^1$H NMR (400 MHz, CD$_3$OD) δ 7.55 (m, 2H), 7.46 (m, 3H), 7.10 (t, J=7.9 Hz, 1H), 6.78 (d, J=7.9 Hz, 1H), 6.74 (dd, J=2.1, 0.8 Hz, 1H), 6.61 (dd, J=7.9, 1.6 Hz, 1H), 4.42 (s, 2H), 3.70 (m, 2H), 3.36 (m, 1H), 2.42 (m, 1H), 2.31 (brd, J=14.5 Hz, 1H), 2.23 (m, 1H), 2.20–210 (m, 3H), 1.94 (m, 1H), 1.84 (m, 2H), 1,70 (m, 1H); $^{13}$C NMR (100 MHz, HCl salt, DMSO$_{d6}$) δ □157.9, 151.8, 131.8, 130.9, 129.9, 129.9, 129.5, 129.4, 115.8, 113.6, 112.3, 56.9, 53.7, 49.6, 37.4, 35.1, 34.2, 34.0, 21.9, 21.2; APCI MS m/z 308.3 (M+1)$^+$.

Trifluoro-methanesulfonic acid 3-(2-benzyl-2-aza-bicyclo[3.3.1]non-5-yl)-phenyl ester 3-(2-Benzyl-2-aza-bicyclo[3.3.1]non-5-yl)-phenol (31.51 g, 102 mmol) was dissolved in CH$_2$Cl$_2$ (250 mL) with triethylamine (20 mL, 143 mmol) and N-phenyltrifluoromethanesulfonimide (43.94 g, 123 mmol). The reaction was judged complete by TLC after 18 h, then quenched with saturated aqueous NaHCO$_3$ solution (100 mL). The product was extracted with CH$_2$Cl$_2$ (3×100 mL), washed with water (200 mL), saturated aqueous NaCl solution (200 mL), dried through a cotton plug and concentrated to an oil. This was filtered through a silica pad (6×6 in), eluted with 15–20% EtOAc/hexanes and concentrated to a semi-solid (37.4 g, 83%). (TLC 25% EtOAc/hexanes R$_f$ 0.30); $^1$H NMR (400 MHz, CDCl$_3$) δ 7.46 (m, 2H), 7.34 (m, 3H), 7.28 (m, 1H), 7.13 (m, 1H), 7.08 (m, 1H), 6.95 (m, 1H), 3.90 (AB q, ΔAB=14.8, J=13.3 Hz, 2H), 3.27 (m, 1H), 3.16 (m, 1H), 3.04 (m, 1H), 2.22 (m, 2H), 2.03 (m, 4H), 1.81 (br d, J=12.9 Hz, 1H), 1.76 (m, 1H), 1.60 (m, 1H), 1.44 (m, 1H); $^{13}$C NMR (100 MHz, CDCl$_3$) δ □ 154.4, 149.9, 130.2, 129.7, 129.0, 128.8, 128.0, 125.2, 125.1, 128.3, 118.2, 59.5, 52.4, 49.3, 38.1, 37.7, 36.5, 35.2, 24.2, 22.4; APCI MS m/z 440.1 (M+1)$^+$.

3-(2-Benzyl-2-aza-bicyclo[3.3.1]non-5-yl)-phenylamine

Trifluoro-methanesulfonic acid 3-(2-benzyl-2-aza-bicyclo[3.3.1]non-5-yl)-phenyl ester (13.33 g, 30.33 mmol) was azeotroped with THF (2×50 mL) then dissolved in anhydrous THF (150 mL) with benzophenone imine (6.3 mL, 17.61 mmol), cesium carbonate (14.23 g, 43.67 mmol) and BINAP (racemic, 1.89 g, 3.03 mmol). The reaction vessel was degassed (evac./N$_2$ purge 3×) before charging with palladium (II) acetate (410 mg, 1.82 mmol). The reaction was warmed to 80° C. for 18 h, at which point it was judged incomplete by APCI MS. After cooling additional BINAP (racemic, 1.89 g, 3.03 mmol) and palladium (II) acetate (410 mg, 1.82 mmol) were introduced and the reaction was warmed to 80° C. for 60 h, at which point it was judged complete by APCI MS. The reaction was cooled and filtered through Celite, rinsed with THF and concentrated. The resulting oil was dissolved in $CH_2Cl_2$ (200 mL), washed with water (100 mL) and saturated aqueous NaCl solution (100 mL), dried through a cotton plug and concentrated to give the crude product. To this was added fresh THF (150 mL) followed by 2N HCl (150 mL) and this stirred solution was warmed to 65° C. for 60 min then at room temperature for 18 h. The reaction mixture was treated with hexanes (150 mL). The resulting orange solid is filtered. (On occasion an orange gum separates and is separated by decantation or filtration.) The biphasic filtrate was separated and the hexane layer discarded. The aqueous layer was extracted with $Et_2O$ (150 mL) and the $Et_2O$ layer discarded. The aqueous layer was then neutralized with 25% aqueous NaOH solution to achieve pH 9 and the product was extracted with $CH_2Cl_2$ (5×40 mL), washed with saturated aqueous NaCl solution (1×30 mL), dried over $Na_2SO_4$ and concentrated to give the crude product. Flash chromatography provided the title compound as a thick yellow oil (3.36 g, 36%). (TLC 50% EtOAc/hexanes $R_f$ 0.30); $^1H$ NMR (400 MHz, $CDCl_3$) δ 7.24 (m, 2H), 7.36 (m, 2H), 7.26 (m, 2H), 7.07 (t, J=7.9 Hz, 1H), 6.71 (dd, J=7.9, 1.6 Hz, 1H), 6.64 (m, 1H), 6.50 (dd, J=7.9, 2.0 Hz, 1H), 3.80 (m, 2H), 3.61 (m, 1H), 3.15 (m, 2H), 2.80 (m, 1H), 2.17 (br d, J=14.2 Hz, 2H), 2.00 (m, 3H), 1.79 (br d, J=12.5 Hz, 1H), 1.72 (m, 1H), 1.64 (m, 1H), 1.38 (m, 1H); APCI MS m/z 307.1 $(M+1)^+$.

2-Methoxy-ethanesulfonic acid [3-(2-benzyl-2-aza-bicyclo[3.3.1]non-5-yl)-phenyl]-amide 3-(2-Benzyl-2-aza-bicyclo[3.3.1]non-5-yl)-phenylamine (2.71 g, 8.84 mmol) stirred in pyridine (25 ml) at 0° C. was charged with 2-methoxy-ethanesulfonyl chloride (2.1 g, 13.26 mmol) dropwise causing a color change from yellow to bright orange. The reaction was allowed to warm to room temperature gradually and stirred 18 h. The reaction mixture was diluted with toluene and concentrated in vacuo. The residue was dissolved in $CH_2Cl_2$ and washed with saturated aqueous $NaHCO_3$ solution (100 mL). The aqueous layer was extracted with $CH_2Cl_2$ (2×50 ml) and the organic layer was concentrated to an oil. This was dissolved in EtOAc which caused an oil to separate. The EtOAc layer was separated and washed with saturated aqueous $NaHCO_3$ solution (100 mL). The aqueous layer was extracted with EtOAc (2×50 ml) and the combined organic layer was washed with saturated aqueous NaCl solution (50 ml), dried over $Na_2SO_4$, filtered and concentrated to a crude orange liquid (3.77 g, ~100%). (TLC 75% EtOAc/hexanes $R_f$ 0.48);

$^1H$ NMR (400 MHz, $CDCl_3$) δ 7.31 (t, J=7.9 Hz, 1H), 7.28–7.15 (m, 6H), 7.14 (br d, J=7.9 Hz, 1H), 7.03 (br d, J=7.9 Hz, 1H), 3.82 (m, 1H), 3.80 (dd, J=5.3, 4.6 Hz, 2H), 3.39 (s, 3H), 3.37 (m, 1H), 3.18 (dd, J=5.3, 4.6 Hz, 2H), 2.30–1.45 (m, 10H); $^{13}C$ NMR (100 MHz, $CDCl_3$) δ 154.0, 137.0, 129.3, 129.1, 128.5, 127.1, 122.4, 119.5, 119.2, 67.0, 60.1, 59.4, 52.3, 50.0, 49.4, 38.8, 38.7, 37.4, 35.3, 25.0, 23.0.

5-[3-(2-Methoxy-ethanesulfonylamino)-phenyl]-2-aza-bicyclo[3.3.1]nonane-2-carboxylic acid tert-butyl ester 2-Methoxy-ethanesulfonic acid [3-(2-benzyl-2-aza-bicyclo[3.3.1]non-5-yl)-phenyl]-amide (3.41 g, 7.96 mmol) was dissolved in EtOAc (20 ml), charged with 2.5 N HCl/EtOAc (6 ml), stripped in vacuo then azeotroped with MeOH (2×50 ml) to yield the HCl salt. This salt was dissolved in MeOH (30 ml). In a separate vessel, MeOH (10 mL) and piperidine (3.9 mL, 39.8 mmol) were stirred at 0° C. and treated with formic acid (0.92 mL, 23.88 mmol) dropwise. This solution was added to the mixture in the first vessel. To the combined mixture was added 20% $Pd(OH)_2/C$ (680 mg) and the resulting mixture was stirred and heated under reflux at 65° C. for 18 h. The reaction was not complete (TLC) at this time. Heating was continued for an additional 60 h at which time it was deemed complete by TLC analysis. The reaction was filtered through a Celite pad and concentrated to afford the crude product that was dissolved in $CH_2Cl_2$ (40 mL) and saturated aqueous $Na_2CO_3$ solution (40 mL) and cooled to 0° C. This was treated with t-Boc$_2$O (di-tert-butyldicarbonate, 2.08 g, 9.55 mmol) in $CH_2Cl_2$ (10 mL) dropwise and the mixture was vigorously stirred for 18 h at ambient temperature. Dilute HCl solution was added to achieve pH 9 and the mixture was extracted with $CH_2Cl_2$ (3×40 mL). The organic layer was washed with saturated aqueous NaCl solution (50 mL), dried through a cotton plug and concentrated to a red oil. This was chromatographed on silica gel eluting with 10 to 30% EtOAc/hexanes to provide product as a clear oil (2.44 g, 70%). (TLC 50% EtOAc/hexanes $R_f$ 0.42); $^1H$ NMR (400 MHz, $CDCl_3$) δ 7.23 (t, J=7.9 Hz, 1H), 7.18 (br s, 1H), 7.12 (br d, J=7.9 Hz, 1H), 7.03 (br d, J=7.9 Hz, 1H), 6.35 (s, NH), 4.31 (m, 1H), 3.81 (t, J=5.6 Hz, 2H), 3.61 (m, 2H), 3.40 (s, 3H), 3.19 (t, J=5.6 Hz, 2H), 2.10 (m, 2H), 1.95 (m, 2H), 1.82 (m, 2H), 1.82 (m, 2H), 1.65 (m, 1H), 1.50–1.35 (m, 3H), 1.44 (s, 9H); APCI MS m/z 424.1 $(M-14)^+$.

2-Methoxy-ethanesulfonic acid [3-(2-aza-bicyclo [3.3.1]non-5-yl)-phenyl]-amide

5-[3-(2-Methoxy-ethanesulfonylamino)-phenyl]-2-aza-bicyclo[3.3.1]nonane-2-carboxylic acid tert-butyl ester (2.42 g, 5.52 mmol) in EtOAc (30 mL) was charged with 2.5 N HCl/EtOAc (30 ml) and the resulting mixture was heated under reflux 18 h. The mixture was stripped in vacuo to yield the HCl salt as a white foam (1.56 g, 83%). $^1H$ NMR (400 MHz, $CD_3OD$, HCl salt) δ 7.28 (t, J=7.9 Hz, 1H), 7.25 (m, 1H), 7.14 (m, 1H), 7.10 (m, 1H), 3.87 (br s, 1H), 3.72 (t, J=5.8 Hz, 2H), 3.71 (m, 1H), 3.27 (t, J=5.8 Hz, 2H), 3.25 (s, 3H), 2.34 (m, 1H), 2.18 (m, 5H), 1.98–1.78 (m, 3H), 1.64 (m, 1H); $^{13}C$ NMR (100 MHz, $CD_3OD$) δ 151.1, 138.4, 129.4, 120.7, 118.6, 117.1, 66.3, 57.9, 50.4, 48.9, 40.5, 36.9, 34.1, 33.8, 33.6, 25.6, 20.7.

Preparation 2

N-[3-(2-Benzyl-2-aza-bicyclo[3.3.1]non-5-yl)-phenyl]-methanesulfonamide 3-(2-Benzyl-2-aza-bicyclo[3.3.1]non-5-yl)-phenylamine (3.37 g, 9.24 mmol) in pyridine (30 ml) at 0° C. was charged with methanesulfonylchloride 1.3 ml, 16.5 mmol) dropwise, causing a color change from yellow to bright orange. The reaction was warmed to room temperature and judged complete by TLC after 3 h. The mixture was diluted with toluene and stripped twice. Following a water quench (20 ml), the product was extracted with EtOAc (4×30 ml), washed with saturated aqueous NaHCO$_3$ solution (6×30 ml) and with saturated aqueous NaCl solution (3×30 ml), dried over Na$_2$SO$_4$, filtered and concentrated to a crude orange liquid. Flash chromatography on silica gel eluting with 2 to 5% MeOH/CH$_2$Cl$_2$ provided the title compound as orange oil (3.59 g, 85%). (TLC 5% MeOH/CH$_2$Cl$_2$ R$_f$ 0.24); $^1$H NMR (400 MHz, CDCl$_3$) δ 7.37–7.19 (m, 7H), 7.11 (br d, J=7.9 Hz, 1H), 7.05 (ddd, J=7.9, 2.1, 0.8 Hz, 1H), 3.73 (AB q, ΔAB 59.9, J=13.3 Hz, 2H), 3.71 (m, 1H), 3.09 (br, s, 1H), 3.04 (m, 1H), 2.94 (s, 3H), 2.80 (m, 1H), 2.18 (m, 2H), 2.07–1.95 (m, 4H), 1.82 (br d, J=12.0 Hz, 1H), 1.72 (m, 1H), 1.57 (m, 1H), 1.17 (m, 1H). $^{13}$C 154.2, 137.1, 132.3, 129.5, 129.4, 129.1, 128.6, 128.4, 127.1, 122.0, 118.3, 117.9, 60.1, 52.3, 49.4, 39.3, 38.9, 38.7, 37.4, 35.8, 24.9, 23.0; APCI MS m/z 385.1 (M+1)$^+$.

5-(3-Methanesulfonylamino-phenyl)-2-aza-bicyclo[3.3.1]nonane-2-carboxylic acid tert-butyl ester N-[3-(2-Benzyl-2-aza-bicyclo[3.3.1]non-5-yl)-phenyl]-methanesulfonamide (3.32 g, 8.63 mmol) (3.41 g, 7.96 mmol) was dissolved in EtOAc (20 ml), charged with 2.5 N HCl/EtOAc (6 ml), stripped in vacuo then azeotroped with MeOH (2×50 ml) to yield the HCl salt. This salt was dissolved in MeOH (30 ml). In a separate vessel, MeOH (10 mL) and piperidine (4.3 mL, 43.15 mmol) were stirred at 0° C. and treated with formic acid (0.99 mL, 25.89 mmol) dropwise. This solution was added to the mixture in the first vessel. To the combined mixture was added 20% Pd(OH)$_2$/C (660 mg) and the resulting mixture was stirred and heated under reflux at 65° C. for 60 h at which time it was deemed complete by TLC analysis. The reaction was filtered through a Celite pad and concentrated to afford the crude product that was dissolved in CH$_2$Cl$_2$ (40 mL) and saturated aqueous Na$_2$CO$_3$ solution (40 mL) and cooled to 0° C. This was treated with t-Boc$_2$O (di-tert-butyldicarbonate, 2.26 g, 10.36 mmol) in CH$_2$Cl$_2$ (10 mL) dropwise and the mixture was vigorously stirred for 2 h at ambient temperature. The reaction was deemed incomplete at this time and was treated with t-Boc$_2$O (di-tert-butyldicarbonate, 950 mg, 4.32 mmol) in CH$_2$Cl$_2$ (10 mL) dropwise and the mixture was vigorously stirred for 18 h. Dilute HCl solution was added to achieve pH 9 and the mixture was extracted with CH$_2$Cl$_2$ (3×40 mL). The organic layer was washed with saturated aqueous NaCl solution (50 mL), dried through a cotton plug and concentrated to an oil. This was chromatographed on silica gel eluting with a gradient from 5 to 25% EtOAc/hexanes to provide product as a clear oil (1.18 g, 35%). (TLC 50% EtOAc/hexanes R$_f$ 0.39); APCI MS m/z 336.2 (M–57)$^+$; 380.2 (M–14)$^+$.

N-[3-(2-Aza-bicyclo[3.3.1]non-5-yl)-phenyl]-methanesulfonamide 5-(3-Methanesulfonylamino-phenyl)-2-aza-bicyclo[3.3.1]nonane-2-carboxylic acid tert-butyl ester (1.07 g, 2.71 mmol) in EtOAc (10 ml) was charged with 2.5 N HCl/EtOAc (10 ml) and the resulting mixture was heated under reflux 18 h. The mixture was stripped in vacuo and recrystallized from MeOH/Et$_2$O to yield the HCl salt (0.64 g, 71%). $^1$H NMR (400 MHz, CD$_3$OD, HCl salt) δ 7.30 (t, J=7.9 Hz, 1H), 7.25 (t, J=2.0 Hz, 1H), 7.15 (ddd, J=7.9, 2.0, 0.8 Hz, 1H), 7.09 (ddd, J=7.9, 2.0, 0.8 Hz, 1H), 3.86 (br s, 1H), 3.72 (m, 1H), 3.27 (m, 2H), 2.91 (s, 3H), 2.35 (m, 1H), 2.18 (m, 5H), 1.91 (m, 3H), 1.67 (m, 1H); APCI MS m/z 295.2 (M+1)$^+$.

Preparation 3

3-(2-Benzyl-2-aza-bicyclo[3.3.1]non-5-yl)-benzonitrile

Trifluoro-methanesulfonic acid 3-(2-benzyl-2-aza-bicyclo[3.3.1]non-5-yl)-phenyl ester (5.00 g, 11.4 mmol) and zinc cyanide (1.47 g, 12.5 mmol) were combined in DMF (110 ml), degassed (evac./N$_2$ purge 3×) then charged with tetrakis(triphenylphosphine) palladium (0) (1.8 g, 1.60 mmol). The resulting reaction mixture was heated to 85° C. in an oil bath for 6 h. Upon cooling to room temperature, the reaction mixture was filtered through a Celite pad and rinsed with EtOAc (200 ml). The filtrate was washed with water and saturated aqueous NaCl solution (1×200 ml each), dried over Na$_2$SO$_4$, filtered, and concentrated and chromatographed on silica gel eluting with 50% EtOAc/hexanes to provide an oil (1.95 g, 54%). (TLC 50% EtOAc/hexanes R$_f$ 0.28); $^1$H NMR (400 MHz, CDCl$_3$) δ 7.49–7.52 (m, 2H), 7.45–7.48 (m, 3H), 7.35–7.39 (m, 2H), 7.10–7.14 (m, 1H), 7.00–7.02 (m, 1H), 3.98 (ABq, □AB=48.9 Hz, J=13.0 Hz, 2H), 3.31–3.33 (m, 1H), 3.16–3.21 (m, 2H), 2.21–2.25 (m, 2H), 1.95–2.07 (m, 4H), 1.76–1.80 (m, 2H), 1.41–1.59 (m, 2H); APCI MS m/z 317.2 (M+1)$^+$.

3-(2-Benzyl-2-aza-bicyclo[3.3.1]non-5-yl)-benzamide 3-(2-Benzyl-2-aza-bicyclo[3.3.1]non-5-yl)-benzonitrile (1.95 g, 6.16 mmol) in DMSO (55 ml) was charged with potassium carbonate (120 mg, 0.86 mmol) then 30% aqueous hydrogen peroxide (3.2 ml, 30.8 mmol). The reaction mixture was allowed to stir at room temperature for 23 h at which time it was determined not to have proceeded. Additional potassium carbonate (850 mg, 6.16 mmol) and 30% aqueous hydrogen peroxide (6.4 ml, 61.6 mmol) were introduced and stirred for 5.5 h. After a water quench (50 ml), the product was extracted with EtOAc (3×50 ml), washed with 50% saturated aqueous NaCl solution (5×50 ml), dried over Na$_2$SO$_4$, filtered and concentrated to a white solid which was triturated with hexanes and collected (1.0 g, 49%). (TLC 50% EtOAc/hexanes R$_f$ 0.08); $^1$H NMR (400 MHz, CDCl$_3$) δ 7.83–7.85 (m, 1H), 7.49–7.57 (m, 1H), 7.40–7.47 (m, 1H), 7.38–7.28 (m, 5H), 7.21–7.25 (m, 1H), 6.10 (brs, 1H), 5.63 (brs, 1H); 3.74–3.82 (m, 2H), 3.06–3.15 (m, 2H), 2.86–2.96 (m, 1H), 2.16–2.26 (m, 2H), 1.96–2.08 (m, 4H), 1.84–1.89 (m, 1H), 1.68–1.74 (m, 1H), 1.59–1.65 (m, 1H), 1.34–1.42 (m, 1H); APCI MS m/z 335.1 (M+1)$^+$.

3-(2-Aza-bicyclo[3.3.1]non-5-yl)-benzamide 3-(2-Benzyl-2-aza-bicyclo[3.3.1]non-5-yl)-benzamide (920 mg, 2.61 mmol) was dissolved in EtOAc (20 ml), charged with 2.5 N HCl/EtOAc (6 ml), then azeotroped with MeOH (2×50 ml) to yield the HCl salt. This salt was dissolved in MeOH (20 ml) in a 500 ml Parr bottle. To this was added 20% Pd(OH)$_2$/C (Pearlman's catalyst, 180 mg) and the mixture was shaken under 45 psi of H$_2$ for 4 h or until judged complete by TLC. The reaction was filtered through a Celite pad and concentrated to a yellow solid (1.0 g, >100%). $^1$H NMR (400 MHz, CD$_3$OD, HCl salt) δ

7.86–7.88 (m, 1H), 7.72–7.74 (m, 1H), 7.55–7.57 (m, 1H), 7.42 (t, J=7.88 Hz, 1H), 3.87 (brs, 1H), 3.71–3.73 (m, 1H), 3.28–3.31 (m, 1H), 2.35–2.37 (m, 1H), 2.13–2.25 (m, 5H), 1.81–1.96 (m, 4H); APCI MS 245.1 (M+1)$^+$.

General Procedures

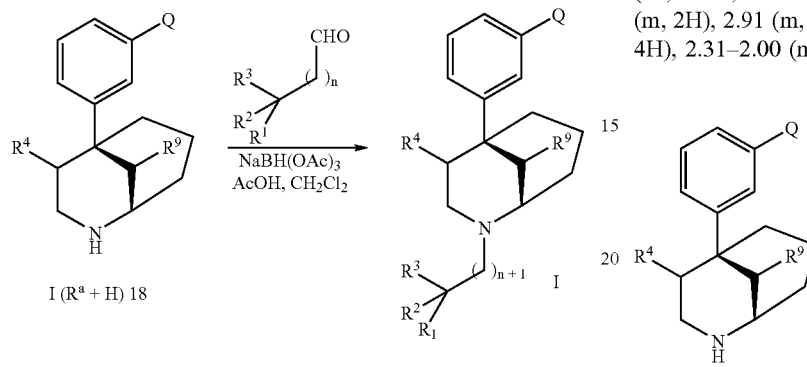

General Procedure for the Reductive Alkylation of Compounds of Formula I R$^a$=H A compound of the general formula I where R$^a$=H in dichloromethane or dichloroethane (0.2 M) at room temperature was treated with an appropriate aldehyde of formula (1.2 equiv), glacial acetic acid (catalytic ~2 drops) and sodium triacetoxyborohydride (1.5 equiv). The reaction mixture was stirred at room temperature for up to 24 h. The mixture was concentrated in vacuo and the resulting crude material was purified by flash chromatography to yield the desired tertiary amines in 40–95%.

The following compounds were made using the above procedure, starting with the appropriate starting amine and the appropriate corresponding aldehyde reagent.

Furthermore, pharmaceutically acceptable salts of the compounds listed below can be prepared as follows. To a stirring solution of compounds of the general formula I (prepared as described above, 1.0 equiv) in a suitable solvent such as methyl ethyl ketone, dichloromethane/methanol (1:1) or methanol (0.1 M) at room temperature was added the appropriate acid, such as citric acid, p-toluenesulfonic acid, methanesulfonic acid or benzene sulfonic acid (1.0 equiv) in one portion. The resulting mixture was stirred at room temperature for up to 18 h, during which time a precipitate formed. Filtration of the solid and drying under reduced pressure afforded the desired salts.

Example 1

N-[3-(2-Cyclopropylmethyl-2-aza-bicyclo[3.3.1]non-5-yl)-phenyl]-methanesulfonamide $^1$H NMR (400 MHz, CD$_3$OD, HCl salt) δ 7.30 (t, J=7.9 Hz, 1H), 7.26 (m, 1H), 7.15 (dd, J=7.9, 2.1 Hz, 1H), 7.07 (m, 1H), 3.97 (br s, 1H), 3.58 (m, 2H), 3.27 (m, 1H), 3.01 (dd, J=13.3, 8.2 Hz, 1H), 2.91 (s, 3H), 2.40–1.62 (m, 1OH), 1.84 (m, 1H), 0.74 (m, 2H), 0.45 (m, 2H); APCI MS m/z 349.2 (M+1)$^+$.

Example 2

N-(3-{2-[3-(1-Hydroxy-cyclohexyl)-propyl]-2-aza-bicyclo[3.3.1]non-5-yl}-phenyl)-methanesulfonamide $^1$H NMR (400 MHz, CD$_3$OD, Citrate salt) δ 7.28 (t, J=7.9 Hz, 1H), 7.23 (m, 1H), 7.14 (dd, J=7.9, 0.8 Hz, 1H), 7.09 (dd, J=7.9, 1.3 Hz, 1H), 3.84 (br s, 1H), 3.54 (m, 2H), 3.17 (m, 2H), 2.91 (m, 3H), 2.76 (AB q, AB Δ=27.9, J=15.8 Hz, 4H), 2.31–2.00 (m, 5H), 1.82 (m, 3H), 1.70–1.23 (m, 8H).

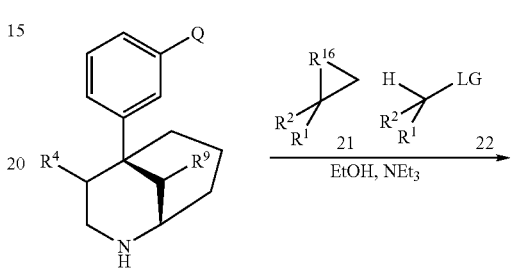

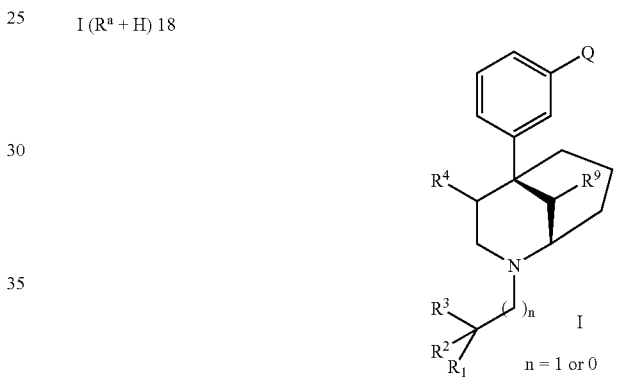

General Procedure for the Alkylation of Compounds of Formula I where R$^a$=H

A compound of formula I where R$^a$=H in ethanol (0.1 M) at room temperature was treated with triethylamine (3.0 equiv) and the appropriate alkylation reagent (1.2 equiv). The resulting mixture was heated to 80° C. for 1–5 h and then cooled to room temperature. The mixture was concentrated in vacuo and the resulting crude material was purified by flash chromatography to yield the desired tertiary amines in 50–90% yield The following compounds were made using the above procedure, starting with the appropriate starting amine and the appropriate alkylation reagent.

Furthermore, pharmaceutically acceptable salts of the compounds listed below can be prepared as follows. To a stirring solution of compounds of the general formula I (prepared as described above, 1.0 equiv) in a suitable solvent such as methyl ethyl ketone, dichloromethane/methanol (1:1) or methanol (0.1 M) at room temperature was added the appropriate acid, such as citric acid, p-toluenesulfonic acid, methanesulfonic acid or benzene sulfonic acid (1.0 equiv) in one portion. The resulting mixture was stirred at room temperature for up to 18 h, during which time a precipitate formed. Filtration of the solid and drying under reduced pressure afforded the desired salts.

Example 3

N-{3-[2-(2-Hydroxy-indan-2-ylmethyl)-2-aza-bicyclo[3.3.1]non-5-yl]-phenyl}-methanesulfonamide $^1$H NMR (400 MHz, CD$_3$OD 27.9 salt) δ 7.29 (t, 7.9 Hz, 1H), 7.25 (m, 1H), 7.26–7.07 (m, 6H), 3.88 (br s, 1H), 3.57 (m, 1H), 3.49–3.39 (m, 3H), 3.18 (AB d, J=16.2 Hz, 2H), 3.08 (AB dd, J=16.2, 4.1 Hz, 2H), 2.91 (s, 3H), 2.70 (AB q, ΔAB=27.9, J=15.4 Hz, 2H), 2.44 (m, 1H), 2.36 (m, 1H), 2.25 (m, 1H), 2.14 (m, 3H), 1.83 (m, 2H), 1.71 (m, 1H); APCI MS m/z 441.2 (M+1)$^+$.

General Procedure (a) for the Reductive Alkylation of Salts of Compounds of Formula I (R$^a$=H)

An appropriate aldehyde (2.0 equiv) in dichloroethane (0.1 M) at room temperature was treated with triethylamine (4.0 equiv) and an amine of formula I R$^a$=H (1 equiv) as the HCl salt. The reaction vessel was sealed and briefly shaken to mix these materials. The vessel was then opened and sodium triacetoxyborohydride (approximately 2.0 or more equiv) was introduced. The reaction vessel was again sealed then briefly vortexed. The reaction vessel was then shaken at room temperature for up to 24 h. The mixture was then quenched with the addition of 1 N NaOH (2.0 mL) and extracted with dichloromethane (3×2.45 mL). Each sequential extract was loaded onto SPE cartridges that contained 1 g of preconditioned SCX adsorbent. (The SCX adsorbent, "strong cation exchange modified silica", was preconditioned by pre-eluting with methanol (1×5 mL) then dichloromethane (2×5 mL). After the extract solutions were passed through the adsorbent, the adsorbent was washed with methanol (5 mL). These filtrates were eventually discarded. Crude product was then eluted into separate tared collection vessels with 1 N triethylamine in methanol (5 mL). The material was concentrated under a stream of nitrogen and weighed. The resulting crude material was purified by reverse phase HPLC to yield the desired tertiary amines.

The following compounds were made using the above procedure, starting with the appropriate starting amine of formula I (R$^a$=H) and the appropriate aldehyde reagent.

General Procedure (b) for the Reduction Alkylation of Salts of Compounds of Formula I (R$^a$=H)

An appropriate aldehyde (2.0 equiv) at room temperature was treated with a slurry of an amine of formula I R$^a$=H (1 equiv) as the HCl salt in 9:1 dichloroethane:methanol. The reaction vessel was sealed and briefly shaken to mix these materials. The vessel was then opened and sodium triacetoxyborohydride (approximately 5.0 or more equiv) was introduced. The reaction vessel was shaken at room temperature for up to 24 h. The mixtures were then quenched by the addition of water (0.75 mL) and extracted with dichloromethane (3×2.45 mL). Each sequential extract was loaded onto SPE cartridges that contained 1 g of preconditioned SCX absorbant. (The SCX absorbant, "strong cation exchange modified silica", was preconditioned by pre-eluting with MeOH (1×5 mL) then dichloromethane (2×5 mL). After the extract solutions were passed through the adsorbent, the adsorbent was washed with dichloromethane (5 mL) then methanol (5 mL). These filtrates were eventually discarded. Crude product was then eluted into separate tared collection vessels with 1N triethylamine in methanol (5 mL). The material was concentrated under a stream of nitrogen and weighed. The resulting crude material was purified by reverse phase HPLC to yield the desired tertiary amines.

A number of compounds according to the present invention were made using the above procedure, starting with the appropriate starting amine of formula I R$^a$=H and the appropriate aldehyde reagent.

Furthermore, pharmaceutically acceptable salts of the compounds described above can be prepared as follows. To a stirring solution of compounds of the general formula I (prepared as described above, 1.0 equiv) in a suitable solvent such as methyl ethyl ketone, dichloromethane/methanol (1:1) or methanol (0.1 M) at room temperature was added the appropriate acid, such as citric acid, p-toluenesulfonic acid, methanesulfonic acid or benzene sulfonic acid (1.0 equiv) in one portion. The resulting mixture was stirred at room temperature for up to 18 h, during which time a precipitate formed. Filtration of the solid and drying under reduced pressure afforded the desired salts.

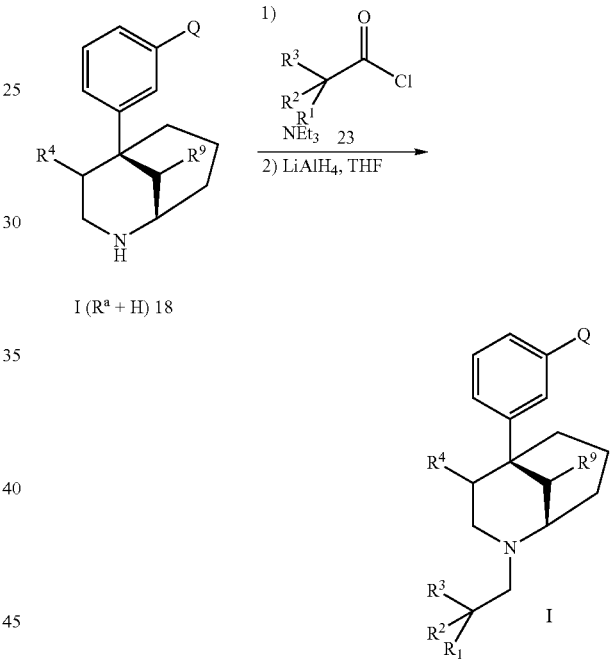

Alternative General Procedure for the Preparation of Compounds of Formula I.

To a stirring solution of 1.0 equiv of a compound of formula I where R$^a$=H in anhydrous THF (0.1 M) at room temperature, was added Et$_3$N (5.0 equiv) or pyridine (5.0 equiv) and an appropriately substituted acid chloride (2.0 equiv). After stirring up to 24 h, the reaction was quenched by the addition of water and diluted with methylene chloride. The layers were separated, the aqueous layer was extracted with methylene chloride and the combined organic layers were dried over anhydrous Na$_2$SO$_4$ and concentrated. The resulting crude material was purified through flash chromatography, then carried onto the next step.

To a stirring solution of 1.0 equiv of the amide prepared above in THF (0.2M) at room temperature was added lithium aluminum hydride (4.0 equiv). The resulting mixture was stirred at room temperature until judged complete by TLC. The reaction was cooled to 0° C. then carefully quenched by the slow addition of water (1.0 equiv by mass relative to LAH), 10% NaOH (1.0 equiv by mass relative to LAH) then water (3.0 equiv by mass relative to LAH). The resulting slurry was stirred at room temperature for up to 16 hours. The slurry was filtered and washed with THF. The resulting solution was concentrated to yield crude material that was purified by flash chromatography to afford the desired tertiary amines of formula I.

The following compound was made using the above procedure, starting with the appropriate starting amine of formula I and the appropriate acid chloride reagent.

Furthermore, pharmaceutically acceptable salts of the compounds listed below can be prepared as follows. To a stirring solution of compounds of the general formula I (prepared as described above, 1.0 equiv.) in a suitable solvent such as methyl ethyl ketone, methylene chloride/methanol (1:1) or methanol (0.1 M) at room temperature was added the appropriate acid, such as citric acid, p-toluenesulfonic acid, methansulfonic acid or benzene sulfonic acid (1.0 equiv) in one portion. The resulting mixture was stirred at room temperature for up to 18 h, during which time a precipitate formed. Filtration of the solid and drying under reduced pressure afforded the desired salts.

What is claimed is:

1. A compound of formula I:

formula I

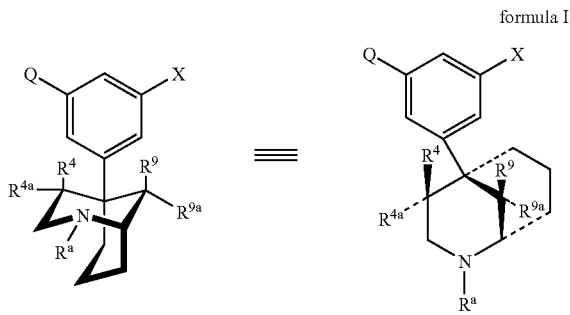

wherein $R^a$ is H or a

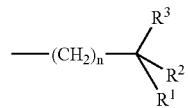

group;

wherein X is H, halogen, —CN, —C≡C—$R^{3a}$ or a —$C_1$–$C_4$ alkyl group optionally substituted with from one to three halogen atoms;

Q is halogen, a $C_1$–$C_6$ alkyl, —CN, —$NH_2$, —NH($C_1$–$C_4$ alkyl), —N($C_1$–$C_4$ alkyl)($C_1$–$C_4$ alkyl), —C(=O)$NH_2$, —C(=O)NH($C_1$–$C_4$ alkyl), —C(=O)N($C_1$–$C_4$ alkyl) ($C_1$–$C_4$ alkyl), —NHC(=O)H, —NHC(=O)$R^8$, or —NHS(=O)$_2R^8$;

$R^1$ and $R^2$ are independently H, a $C_1$–$C_6$ alkyl, —$(CH_2)_j$-aryl, —$(CH_2)_j$-heteroaryl, wherein said alkyl, —$(CH_2)_j$-aryl or —$(CH_2)_j$-heteroaryl group is optionally substituted with one or more $R^{10}$ groups, or with the carbon to which $R^1$ and $R^2$ are attached, $R^1$ and $R^2$ form a $C_3$–$C_7$ carbocyclic or 4- to 7-membered heterocyclic group, wherein said heterocyclic group comprises from one to three heteroatoms selected from the group consisting of O, S and N and said carbocyclic or heterocyclic group optionally contains a —C(=O) group or optionally contains one or more double bonds and is optionally fused to or substituted with a $C_6$–$C_{14}$ aryl or a 5–14 membered heteroaryl group; wherein said $C_3$–$C_7$ carbocyclic or 4- to 7-membered heterocyclic group formed by $R^1$ and $R^2$ may optionally be substituted with from one to three $R^{10}$ groups, and said optionally fused or substituted aryl or heteroaryl group may each optionally independently be substituted with from one to six $R^{10}$ groups;

$R^{10}$ groups are independently selected from $R^{11}$, H, halogen, —$OR^{11}$, —$NO_2$, —CN, —$C_1$–$C_6$ alkyl, —$C_3$–$C_6$ cycloalkyl, —$C(R^3)R^{10a}R^{10b}$, aryl optionally substituted with from 1 to 3 $R^3$ groups, —$(CH_2)_v$—$NR^{11}R^{12}$, —$NR^{11}C(=O)R^{12}$, —$C(=O)NR^{11}R^{12}$, —OC(=O)$R^{11}$, —C(=O)$OR^{11}$, C(=O)$R^{11}$, —$NR^{11}C(=O)OR^{12}$, —$NR^{11}C(=O)NR^{12}R^{13}$, —$NR^{12}S(=O)_2R^{11}$, —$NR^{11}S(=O)_2NR^{12}R^{13}$, and —$S(=O)_2R^{11}$;

$R^3$ is absent or is H, —$C_1$–$C_4$ alkyl, which optionally contains one or two unsaturated bonds, —OH, —O($C_1$–$C_4$)alkyl, —($C_1$–$C_4$)alkylOH, —$(CH_2)_n$—$NR^{10a}R^{10b}$, —$(CH_2)_n$—NHC(=O)($C_1$–$C_4$ alkyl), —$(CH_2)_n$—$NO_2$, —$(CH_2)_n$—C≡N, —$(CH_2)_n$—C(=O)$NH_2$, —$(CH_2)_n$—C(=O)NH($C_1$–$C_4$ alkyl) or —$(CH_2)_v$—C(=O)$NR^{10a}R^{10b}$;

$R^{3a}$ is H or $C_1$–$C_6$ alkyl which may be optionally substituted with one or more halogen groups;

each $R^4$, $R^{4a}$, $R^9$ and $R^{9a}$ is independently H, —$C_1$–$C_4$ alkyl or —O—$C_1$–$C_4$ alkyl;

each $R^8$, $R^{11}$, $R^{12}$ and $R^{13}$ is independently selected from H, —$C_1$–$C_6$ alkyl, $C_3$–$C_6$ cycloalkyl, aryl, —($C_2$–$C_4$ alkyl)—O—($C_1$–$C_4$alkyl), aryl, —$(CH_2)_m$—$NR^{14}R^{15}$, or a 4- to 7-membered heterocyclic group, or where any two groups selected from $R^{11}$, $R^{12}$ and $R^{13}$ can form a heterocyclic ring with the atom to which they are attached, wherein said heterocyclic group or said heterocyclic ring is optionally substituted with at least one $C_1$–$C_4$ alkyl group;

each $R^{10a}$ and $R^{10b}$ is independently selected from H, —$C_1$–$C_4$ alkyl; or, independently in each instance of —$C(R^3)R^{10a}R^{10b}$, $R^{10a}$ and $R^{10b}$ connect to form a $C_3$–$C_7$ carbocyclic ring or a 4–7 membererd heterocyclic ring or in each instance of —$(CH_2)_v$—C(=O) $NR^{10a}R^{10b}$, $R^{10a}$ and $R^{10b}$ connect to form a 4–7 membererd heterocyclic ring;

$R^{14}$ and $R^{15}$ are independently H, $C_1$–$C_6$ alkyl or together may form a 4- to 7-membered carbocyclic or heterocyclic ring;

j is in each instance independently an integer from 0 to 5;
m is 0 or an independently variable integer 2 or greater;
n is in each instance independently an integer from 0 to 5;
v is in each instance independently an integer from 0 to 5;
and pharmaceutically acceptable salts thereof, with the provisos that
a) when $R^a$ is

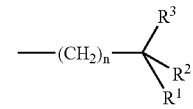

and n is 0, and when the carbon to which $R^1$, $R^2$ and $R^3$ are bound is sp$^3$ hybridized (i.e., "saturated"), then none of $R^1$, $R^2$ and $R^3$ can be a heteroatom or contain a heteroatom which is directly linked to the carbon of said

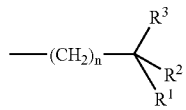

group;
b) $R^8$ cannot be H when part of a —NHS(=O)$_2$R$^8$ group, $R^{11}$ cannot be H when part of a —NR$^{12}$S(=O)$_2$R$^{11}$ and —S(=O)$_2$R$^{11}$; and
c) v of —(CH$_2$)$_v$— cannot be 1 when said methylene unit is connected to N, O or S.

2. A compound according to claim 1 wherein R$^a$ is a

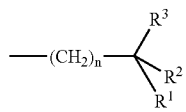

group.

3. A compound according to claim 1 wherein Q is —C(=O)NH$_2$ or —NHSO$_2$R$^8$.

4. A compound according to claim 1 wherein Q is —NHSO$_2$R$^8$.

5. A compound according to claim 3, wherein R$^a$ is a

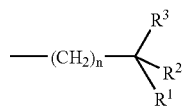

group.

6. A compound according to claim 1 or 2 wherein X is H or F.

7. A compound according to claim 6 wherein Q is —C(=O)NH$_2$ or —NHSO$_2$R$^8$.

8. A compound according to claim 1 wherein R$^1$ and R$^2$ taken together with the carbon to which they are attached form a cyclobutane, cyclopentane, cyclohexane, indane-2-yl or 1,2,3,4-tetrahydronaphth-2-yl, which may be unsubstituted or substituted with R$^{10}$ groups.

9. A compound according to claim 8 wherein Q is —C(=O)NH$_2$ or —NHSO$_2$R$^8$.

10. A compound according to claim 1, wherein Q is —C(=O)NH$_2$ or —NHSO$_2$R$^8$; R$^a$ is a

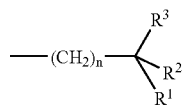

group; and R$^1$ and R$^2$ taken together with the carbon to which they are attached form a cyclobutane, cyclopentane, cyclohexane, indane-2-yl or 1,2,3,4-tetrahydronaphth-2-yl which may be unsubstituted or substituted with R$^{10}$ groups.

11. A compound according to claim 10 wherein R$^3$ is H, OH, —NH(=O)—CH$_3$, —C(=O)NH$_2$, —CH$_2$OH or —OCH$_3$.

12. A compound according to claim 10 wherein R$^3$ is OH.

13. A compound according to claim 2 wherein n is 1, 2 or 3.

14. A compound according to claim 1 wherein R$^4$ and R$^9$ are independently H or a —C$_1$-C$_4$ alkyl.

15. A compound according to claim 1 wherein R$^4$ and R$^9$ are independently H or CH$_3$.

16. A compound according to claim 1 wherein R$^4$ and R$^9$ are both CH$_3$.

17. A compound according to claim 1 wherein Q is —C(=O)NH$_2$ or —NHSO$_2$R$^8$ and R$^8$ is CH$_3$, —(CH$_2$)$_2$—O—CH$_3$ or -4-(1-methylimidazole).

18. A compound according to claim 1 wherein Q is —C(=O)NH$_2$, —NHSO$_2$CH$_3$ or —NHSO$_2$CH$_2$CH$_2$OCH$_3$ and X is H.

19. A compound according to claim 1 selected from:
3-(2-Ethyl-2-aza-bicyclo[3.3.1]non-5-yl)-benzamide;
3-(2-Cyclopropylmethyl-2-aza-bicyclo[3.3.1]non-5-yl)-benzamide;
3-(2-Isobutyl-2-aza-bicyclo[3.3.1]non-5-yl)-benzamide;
3-[2-(3-Methyl-butyl)-2-aza-bicyclo[3.3.1]non-5-yl]-benzamide;
3-(2-Pentyl-2-aza-bicyclo[3.3.1]non-5-yl)-benzamide;
3-[2-(1H-Pyrrol-2-ylmethyl)-2-aza-bicyclo[3.3.1]non-5-yl]-benzamide;
3-[2-(1H-Imidazol-2-ylmethyl)-2-aza-bicyclo[3.3.1]non-5-yl]-benzamide;
3-[2-(1-Hydroxy-cyclobutylmethyl)-2-aza-bicyclo[3.3.1]non-5-yl]-benzamide;
3-(2-Hexyl-2-aza-bicyclo[3.3.1]non-5-yl)-benzamide;
3-[2-(2-Ethyl-butyl)-2-aza-bicyclo[3.3.1]non-5-yl]-benzamide;
3-[2-(1-Methyl-1H-pyrrol-2-ylmethyl)-2-aza-bicyclo[3.3.1]non-5-yl]-benzamide;
3-(2-Thiophen-3-ylmethyl-2-aza-bicyclo[3.3.1]non-5-yl)-benzamide;
3-(2-Thiazol-2-ylmethyl-2-aza-bicyclo[3.3.1]non-5-yl)-benzamide;
3-[2-(1-Hydroxymethyl-cyclobutylmethyl)-2-aza-bicyclo[3.3.1]non-5-yl]-benzamide;
3-(2-Heptyl-2-aza-bicyclo[3.3.1]non-5-yl)-benzamide;
3-(2-Phenethyl-2-aza-bicyclo[3.3.1]non-5-yl)-benzamide;
3-[2-(3-Cyclopentyl-propyl)-2-aza-bicyclo[3.3.1]non-5-yl]-benzamide;
3-[2-(2-Ethyl-hexyl)-2-aza-bicyclo[3.3.1]non-5-yl]-benzamide;
3-(2-Octyl-2-aza-bicyclo[3.3.1]non-5-yl)-benzamide;
3-[2-(3-Phenyl-prop-2-ynyl)-2-aza-bicyclo[3.3.1]non-5-yl]-benzamide;
3-[2-(3-Phenyl-propyl)-2-aza-bicyclo[3.3.1]non-5-yl]-benzamide;
3-[2-(4-Methoxy-benzyl)-2-aza-bicyclo[3.3.1]non-5-yl]-benzamide;
3-[2-(3-Cyclohexyl-propyl)-2-aza-bicyclo[3.3.1]non-5-yl]-benzamide;
3-{2-[3-(1-Hydroxy-cyclopentyl)-propyl]-2-aza-bicyclo[3.3.1]non-5-yl}-benzamide;
3-[2-(1H-Indol-3-ylmethyl)-2-aza-bicyclo[3.3.1]non-5-yl]-benzamide;
3-(2-Benzofuran-2-ylmethyl-2-aza-bicyclo[3.3.1]non-5-yl)-benzamide;
3-(2-Indan-2-ylmethyl-2-aza-bicyclo[3.3.1]non-5-yl)-benzamide;
3-(2-Naphthalen-2-ylmethyl-2-aza-bicyclo[3.3.1]non-5-yl)-benzamide;
3-(2-Naphthalen-1-ylmethyl-2-aza-bicyclo[3.3.1]non-5-yl)-benzamide;
3-{2-[3-(1-Hydroxy-cyclohexyl)-propyl]-2-aza-bicyclo[3.3.1]non-5-yl}-benzamide;

3-{2-[3-(1-Hydroxymethyl-cyclopentyl)-propyl]-2-aza-bicyclo[3.3.1]non-5-yl}-benzamide;
3-(2-Quinolin-4-ylmethyl-2-aza-bicyclo[3.3.1]non-5-yl)-benzamide;
3-(2-Quinolin-3-ylmethyl-2-aza-bicyclo[3.3.1]non-5-yl)-benzamide;
3-[2-(4-Chloro-2-fluoro-benzyl)-2-aza-bicyclo[3.3.1]non-5-yl]-benzamide;
3-[2-(1-Methyl-1H-indol-3-ylmethyl)-2-aza-bicyclo[3.3.1]non-5-yl]-benzamide;
3-[2-(1,2,3,4-Tetrahydro-naphthalen-2-ylmethyl)-2-aza-bicyclo[3.3.1]non-5-yl]-benzamide;
3-[2-(3-Phenyl-cyclobutylmethyl)-2-aza-bicyclo[3.3.1]non-5-yl]-benzamide;
3-[2-(2-Hydroxy-indan-2-ylmethyl)-2-aza-bicyclo[3.3.1]non-5-yl]-benzamide;
3-[2-(2-Phenethyloxy-ethyl)-2-aza-bicyclo[3.3.1]non-5-yl]-benzamide;
3-[2-(4-Hydroxy-naphthalen-1-ylmethyl)-2-aza-bicyclo[3.3.1]non-5-yl]-benzamide;
3-[2-(3-Indan-2-yl-propyl)-2-aza-bicyclo[3.3.1]non-5-yl]-benzamide;
3-[2-(4-Pyrrolidin-1-yl-benzyl)-2-aza-bicyclo[3.3.1]non-5-yl]-benzamide;
3-[2-(2-Hydroxy-1,2,3,4-tetrahydro-naphthalen-2-ylmethyl)-2-aza-bicyclo[3.3.1]non-5-yl]-benzamide;
3-[2-(1-Hydroxy-3-phenyl-cyclobutylmethyl)-2-aza-bicyclo[3.3.1]non-5-yl]-benzamide;
3-[2-(3-Methyl-benzo[b]thiophen-2-ylmethyl)-2-aza-bicyclo[3.3.1]non-5-yl]-benzamide;
3-{2-[2-(4-Chloro-phenyl)-2-cyano-ethyl]-2-aza-bicyclo[3.3.1]non-5-yl}-benzamide;
3-(2-Biphenyl-4-ylmethyl-2-aza-bicyclo[3.3.1]non-5-yl)-benzamide;
3-[2-(3-Trifluoromethoxy-benzyl)-2-aza-bicyclo[3.3.1]non-5-yl]-benzamide;
3-{2-[3-(2-Hydroxy-indan-2-yl)-propyl]-2-aza-bicyclo[3.3.1]non-5-yl}-benzamide;
3-[2-(9H-Fluoren-2-ylmethyl)-2-aza-bicyclo[3.3.1]non-5-yl]-benzamide;
3-[2-(3-Phenoxy-benzyl)-2-aza-bicyclo[3.3.1]non-5-yl]-benzamide; and
3-[2-(4-Dimethylamino-naphthalen-1-ylmethyl)-2-aza-bicyclo[3.3.1]non-5-yl]-benzamide;
and pharmaceutically acceptable salts thereof.

20. A compound according to claim 1 selected from:
N-[3-(2-Ethyl-2-aza-bicyclo[3.3.1]non-5-yl)-phenyl]-methanesulfonamide;
N-[3-(2-Cyclopropylmethyl-2-aza-bicyclo[3.3.1]non-5-yl)-phenyl]-methanesulfonamide;
N-[3-(2-Isobutyl-2-aza-bicyclo[3.3.1]non-5-yl)-phenyl]-methanesulfonamide;
N-{3-[2-(3-Methyl-butyl)-2-aza-bicyclo[3.3.1]non-5-yl]-phenyl}-methanesulfonamide;
N-[3-(2-Pentyl-2-aza-bicyclo[3.3.1]non-5-yl)-phenyl]-methanesulfonamide;
N-{3-[2-(1H-Pyrrol-2-ylmethyl)-2-aza-bicyclo[3.3.1]non-5-yl]-phenyl}-methanesulfonamide;
N-{3-[2-(1H-Imidazol-2-ylmethyl)-2-aza-bicyclo[3.3.1]non-5-yl]-phenyl}-methanesulfonamide;
N-{3-[2-(1-Hydroxy-cyclobutylmethyl)-2-aza-bicyclo[3.3.1]non-5-yl]-phenyl}-methanesulfonamide;
N-[3-(2-Hexyl-2-aza-bicyclo[3.3.1]non-5-yl)-phenyl]-methanesulfonamide;
N-{3-[2-(2-Ethyl-butyl)-2-aza-bicyclo[3.3.1]non-5-yl]-phenyl}-methanesulfonamide;
N-{3-[2-(1-Methyl-1H-pyrrol-2-ylmethyl)-2-aza-bicyclo[3.3.1]non-5-yl]-phenyl}-methanesulfonamide;
N-[3-(2-Thiophen-3-ylmethyl-2-aza-bicyclo[3.3.1]non-5-yl)-phenyl]-methanesulfonamide;
N-[3-(2-Thiazol-2-ylmethyl-2-aza-bicyclo[3.3.1]non-5-yl)-phenyl]-methanesulfonamide;
N-{3-[2-(1-Hydroxymethyl-cyclobutylmethyl)-2-aza-bicyclo[3.3.1]non-5-yl]-phenyl}-methanesulfonamide;
N-[3-(2-Heptyl-2-aza-bicyclo[3.3.1]non-5-yl)-phenyl]-methanesulfonamide;
N-[3-(2-Phenethyl-2-aza-bicyclo[3.3.1]non-5-yl)-phenyl]-methanesulfonamide;
N-{3-[2-(3-Cyclopentyl-propyl)-2-aza-bicyclo[3.3.1]non-5-yl]-phenyl}-methanesulfonamide;
N-{3-[2-(2-Ethyl-hexyl)-2-aza-bicyclo[3.3.1]non-5-yl]-phenyl}-methanesulfonamide;
N-[3-(2-Octyl-2-aza-bicyclo[3.3.1]non-5-yl)-phenyl]-methanesulfonamide;
N-{3-[2-(3-Phenyl-prop-2-ynyl)-2-aza-bicyclo[3.3.1]non-5-yl]-phenyl}-methanesulfonamide;
N-{3-[2-(3-Phenyl-propyl)-2-aza-bicyclo[3.3.1]non-5-yl]-phenyl}-methanesulfonamide;
N-{3-[2-(4-Methoxy-benzyl)-2-aza-bicyclo[3.3.1]non-5-yl]-phenyl}-methanesulfonamide;
N-{3-[2-(3-Cyclohexyl-propyl)-2-aza-bicyclo[3.3.1]non-5-yl]-phenyl}-methanesulfonamide;
N-(3-{2-[3-(1-Hydroxy-cyclopentyl)-propyl]-2-aza-bicyclo[3.3.1]non-5-yl}-phenyl)-methanesulfonamide;
N-{3-[2-(1H-Indol-3-ylmethyl)-2-aza-bicyclo[3.3.1]non-5-yl]-phenyl}-methanesulfonamide;
N-[3-(2-Benzofuran-2-ylmethyl-2-aza-bicyclo[3.3.1]non-5-yl)-phenyl]-methanesulfonamide;
N-[3-(2-Indan-2-ylmethyl-2-aza-bicyclo[3.3.1]non-5-yl)-phenyl]-methanesulfonamide;
N-[3-(2-Naphthalen-2-ylmethyl-2-aza-bicyclo[3.3.1]non-5-yl)-phenyl]-methanesulfonamide;
N-[3-(2-Naphthalen-1-ylmethyl-2-aza-bicyclo[3.3.1]non-5-yl)-phenyl]-methanesulfonamide;
N-(3-{2-[3-(1-Hydroxy-cyclohexyl)-propyl]-2-aza-bicyclo[3.3.1]non-5-yl}-phenyl)-methanesulfonamide;
N-(3-{2-[3-(1-Hydroxymethyl-cyclopentyl)-propyl]-2-aza-bicyclo[3.3.1]non-5-yl}-phenyl)-methanesulfonamide;
N-[3-(2-Quinolin-4-ylmethyl-2-aza-bicyclo[3.3.1]non-5-yl)-phenyl]-methanesulfonamide;
N-[3-(2-Quinolin-3-ylmethyl-2-aza-bicyclo[3.3.1]non-5-yl)-phenyl]-methanesulfonamide;
N-{3-[2-(4-Chloro-2-fluoro-benzyl)-2-aza-bicyclo[3.3.1]non-5-yl]-phenyl}-methanesulfonamide;
N-{3-[2-(1-Methyl-1H-indol-3-ylmethyl)-2-aza-bicyclo[3.3.1]non-5-yl]-phenyl}-methanesulfonamide;
N-{3-[2-(1,2,3,4-Tetrahydro-naphthalen-2-ylmethyl)-2-aza-bicyclo[3.3.1]non-5-yl]-phenyl}-methanesulfonamide;
N-{3-[2-(3-Phenyl-cyclobutylmethyl)-2-aza-bicyclo[3.3.1]non-5-yl]-phenyl}-methanesulfonamide;
N-{3-[2-(2-Hydroxy-indan-2-ylmethyl)-2-aza-bicyclo[3.3.1]non-5-yl]-phenyl}-methanesulfonamide;
N-{3-[2-(2-Phenethyloxy-ethyl)-2-aza-bicyclo[3.3.1]non-5-yl]-phenyl}-methanesulfonamide;
N-{3-[2-(4-Hydroxy-naphthalen-1-ylmethyl)-2-aza-bicyclo[3.3.1]non-5-yl]-phenyl}-methanesulfonamide;
N-{3-[2-(3-Indan-2-yl-propyl)-2-aza-bicyclo[3.3.1]non-5-yl]-phenyl}-methanesulfonamide;
N-{3-[2-(4-Pyrrolidin-1-yl-benzyl)-2-aza-bicyclo[3.3.1]non-5-yl]-phenyl}-methanesulfonamide;

N-{3-[2-(2-Hydroxy-1,2,3,4-tetrahydro-naphthalen-2-yl-methyl)-2-aza-bicyclo[3.3.1]non-5-yl]-phenyl}-methanesulfonamide;

N-{3-[2-(1-Hydroxy-3-phenyl-cyclobutylmethyl)-2-aza-bicyclo[3.3.1]non-5-yl]-phenyl}-methanesulfonamide;

N-{3-[2-(3-Methyl-benzo[b]thiophen-2-ylmethyl)-2-aza-bicyclo[3.3.1]non-5-yl]-phenyl}-methanesulfonamide;

N-(3-{2-[2-(4-Chloro-phenyl)-2-cyano-ethyl]-2-aza-bicyclo[3.3.1]non-5-yl}-phenyl)-methanesulfonamide;

N-[3-(2-Biphenyl-4-ylmethyl-2-aza-bicyclo[3.3.1]non-5-yl)-phenyl]-methanesulfonamide;

N-{3-[2-(3-Trifluoromethoxy-benzyl)-2-aza-bicyclo[3.3.1]non-5-yl]-phenyl}-methanesulfonamide;

N-(3-{2-[3-(2-Hydroxy-indan-2-yl)-propyl]-2-aza-bicyclo[3.3.1]non-5-yl}-phenyl)-methanesulfonamide;

N-{3-[2-(9H-Fluoren-2-ylmethyl)-2-aza-bicyclo[3.3.1]non-5-yl]-phenyl}-methanesulfonamide;

N-{3-[2-(3-Phenoxy-benzyl)-2-aza-bicyclo[3.3.1]non-5-yl]-phenyl}-methanesulfonamide; and N-{3-[2-(4-Dimethylamino-naphthalen-1-ylmethyl)-2-aza-bicyclo[3.3.1]non-5-yl]-phenyl}-methanesulfonamide;

and pharmaceutically acceptable salts thereof.

21. A compound according to claim 1 selected from:

2-Methoxy-ethanesulfonic acid [3-(2-ethyl-2-aza-bicyclo[3.3.1]non-5-yl)-phenyl]-amide;

2-Methoxy-ethanesulfonic acid [3-(2-cyclopropylmethyl-2-aza-bicyclo[3.3.1]non-5-yl)-phenyl]-amide;

2-Methoxy-ethanesulfonic acid [3-(2-isobutyl-2-aza-bicyclo[3.3.1]non-5-yl)-phenyl]-amide;

2-Methoxy-ethanesulfonic acid {3-[2-(3-methyl-butyl)-2-aza-bicyclo[3.3.1]non-5-yl]-phenyl}-amide;

2-Methoxy-ethanesulfonic acid [3-(2-pentyl-2-aza-bicyclo[3.3.1]non-5-yl)-phenyl]-amide;

2-Methoxy-ethanesulfonic acid {3-[2-(1H-pyrrol-2-ylmethyl)-2-aza-bicyclo[3.3.1]non-5-yl]-phenyl}-amide;

2-Methoxy-ethanesulfonic acid {3-[2-(1H-imidazol-2-ylmethyl)-2-aza-bicyclo[3.3.1]non-5-yl]-phenyl}-amide;

2-Methoxy-ethanesulfonic acid {3-[2-(1-hydroxy-cyclobutylmethyl)-2-aza-bicyclo[3.3.1]non-5-yl]-phenyl}-amide;

2-Methoxy-ethanesulfonic acid [3-(2-hexyl-2-aza-bicyclo[3.3.1]non-5-yl)-phenyl]-amide;

2-Methoxy-ethanesulfonic acid {3-[2-(2-ethyl-butyl)-2-aza-bicyclo[3.3.1]non-5-yl]-phenyl}-amide;

2-Methoxy-ethanesulfonic acid {3-[2-(1-methyl-1H-pyrrol-2-ylmethyl)-2-aza-bicyclo[3.3.1]non-5-yl]-phenyl}-amide;

2-Methoxy-ethanesulfonic acid [3-(2-thiophen-3-ylmethyl-2-aza-bicyclo[3.3.1]non-5-yl)-phenyl]-amide;

2-Methoxy-ethanesulfonic acid [3-(2-thiazol-2-ylmethyl-2-aza-bicyclo[3.3.1]non-5-yl)-phenyl]-amide;

2-Methoxy-ethanesulfonic acid {3-[2-(1-hydroxymethyl-cyclobutylmethyl)-2-aza-bicyclo[3.3.1]non-5-yl]-phenyl}-amide;

2-Methoxy-ethanesulfonic acid [3-(2-heptyl-2-aza-bicyclo[3.3.1]non-5-yl)-phenyl]-amide;

2-Methoxy-ethanesulfonic acid [3-(2-phenethyl-2-aza-bicyclo[3.3.1]non-5-yl)-phenyl]-amide;

2-Methoxy-ethanesulfonic acid {3-[2-(3-cyclopentyl-propyl)-2-aza-bicyclo[3.3.1]non-5-yl]-phenyl}-amide;

2-Methoxy-ethanesulfonic acid {3-[2-(2-ethyl-hexyl)-2-aza-bicyclo[3.3.1]non-5-yl]-phenyl}-amide;

2-Methoxy-ethanesulfonic acid [3-(2-octyl-2-aza-bicyclo[3.3.1]non-5-yl)-phenyl]-amide;

2-Methoxy-ethanesulfonic acid {3-[2-(3-phenyl-prop-2-ynyl)-2-aza-bicyclo[3.3.1]non-5-yl]-phenyl}-amide;

2-Methoxy-ethanesulfonic acid {3-[2-(3-phenyl-propyl)-2-aza-bicyclo[3.3.1]non-5-yl]-phenyl}-amide;

2-Methoxy-ethanesulfonic acid {3-[2-(4-methoxy-benzyl)-2-aza-bicyclo[3.3.1]non-5-yl]-phenyl}-amide;

2-Methoxy-ethanesulfonic acid {3-[2-(3-cyclohexyl-propyl)-2-aza-bicyclo[3.3.1]non-5-yl]-phenyl}-amide;

2-Methoxy-ethanesulfonic acid (3-{2-[3-(1-hydroxy-cyclopentyl)-propyl]-2-aza-bicyclo[3.3.1]non-5-yl}-phenyl)-amide;

2-Methoxy-ethanesulfonic acid {3-[2-(1H-indol-3-ylmethyl)-2-aza-bicyclo[3.3.1]non-5-yl]-phenyl}-amide;

2-Methoxy-ethanesulfonic acid [3-(2-benzofuran-2-ylmethyl-2-aza-bicyclo[3.3.1]non-5-yl)-phenyl]-amide;

2-Methoxy-ethanesulfonic acid [3-(2-indan-2-ylmethyl-2-aza-bicyclo[3.3.1]non-5-yl)-phenyl]-amide;

2-Methoxy-ethanesulfonic acid [3-(2-naphthalen-2-ylmethyl-2-aza-bicyclo[3.3.1]non-5-yl)-phenyl]-amide;

2-Methoxy-ethanesulfonic acid [3-(2-naphthalen-1-ylmethyl-2-aza-bicyclo[3.3.1]non-5-yl)-phenyl]-amide;

2-Methoxy-ethanesulfonic acid (3-{2-[3-(1-hydroxy-cyclohexyl)-propyl]-2-aza-bicyclo[3.3.1]non-5-yl}-phenyl)-amide;

2-Methoxy-ethanesulfonic acid (3-{2-[3-(1-hydroxymethyl-cyclopentyl)-propyl]-2-aza-bicyclo[3.3.1]non-5-yl}-phenyl)-amide;

2-Methoxy-ethanesulfonic acid [3-(2-quinolin-4-ylmethyl-2-aza-bicyclo[3.3.1]non-5-yl)-phenyl]-amide;

2-Methoxy-ethanesulfonic acid [3-(2-quinolin-3-ylmethyl-2-aza-bicyclo[3.3.1]non-5-yl)-phenyl]-amide;

2-Methoxy-ethanesulfonic acid {3-[2-(4-chloro-2-fluoro-benzyl)-2-aza-bicyclo[3.3.1]non-5-yl]-phenyl}-amide;

2-Methoxy-ethanesulfonic acid {3-[2-(1-methyl-1H-indol-3-ylmethyl)-2-aza-bicyclo[3.3.1]non-5-yl]-phenyl}-amide;

2-Methoxy-ethanesulfonic acid {3-[2-(1,2,3,4-tetrahydro-naphthalen-2-ylmethyl)-2-aza-bicyclo[3.3.1]non-5-yl]-phenyl}-amide;

2-Methoxy-ethanesulfonic acid {3-[2-(3-phenyl-cyclobutylmethyl)-2-aza-bicyclo[3.3.1]non-5-yl]-phenyl}-amide;

2-Methoxy-ethanesulfonic acid {3-[2-(2-hydroxy-indan-2-ylmethyl)-2-aza-bicyclo[3.3.1]non-5-yl]-phenyl}-amide;

2-Methoxy-ethanesulfonic acid {3-[2-(2-phenethyloxy-ethyl)-2-aza-bicyclo[3.3.1]non-5-yl]-phenyl}-amide;

2-Methoxy-ethanesulfonic acid {3-[2-(4-hydroxy-naphthalen-1-ylmethyl)-2-aza-bicyclo[3.3.1]non-5-yl]-phenyl}-amide;

2-Methoxy-ethanesulfonic acid {3-[2-(3-indan-2-yl-propyl)-2-aza-bicyclo[3.3.1]non-5-yl]-phenyl}-amide;

2-Methoxy-ethanesulfonic acid {3-[2-(4-pyrrolidin-1-yl-benzyl)-2-aza-bicyclo[3.3.1]non-5-yl]-phenyl}-amide;

2-Methoxy-ethanesulfonic acid {3-[2-(2-hydroxy-1,2,3,4-tetrahydro-naphthalen-2-ylmethyl)-2-aza-bicyclo[3.3.1]non-5-yl]-phenyl}-amide;

2-Methoxy-ethanesulfonic acid {3-[2-(1-hydroxy-3-phenyl-cyclobutylmethyl)-2-aza-bicyclo[3.3.1]non-5-yl]-phenyl}-amide;

2-Methoxy-ethanesulfonic acid {3-[2-(3-methyl-benzo[b]thiophen-2-ylmethyl)-2-aza-bicyclo[3.3.1]non-5-yl]-phenyl}-amide;

2-Methoxy-ethanesulfonic acid (3-{2-[2-(4-chloro-phenyl)-2-cyano-ethyl]-2-aza-bicyclo[3.3.1]non-5-yl}-phenyl)-amide;

2-Methoxy-ethanesulfonic acid [3-(2-biphenyl-4-ylmethyl-2-aza-bicyclo[3.3.1]non-5-yl)-phenyl]-amide;

2-Methoxy-ethanesulfonic acid {3-[2-(3-trifluoromethoxy-benzyl)-2-aza-bicyclo[3.3.1]non-5-yl]-phenyl}-amide;

2-Methoxy-ethanesulfonic acid (3-{2-[3-(2-hydroxy-indan-2-yl)-propyl]-2-aza-bicyclo[3.3.1]non-5-yl}-phenyl)-amide;

2-Methoxy-ethanesulfonic acid {3-[2-(9H-fluoren-2-ylmethyl)-2-aza-bicyclo[3.3.1]non-5-yl]-phenyl}-amide;

2-Methoxy-ethanesulfonic acid {3-[2-(3-phenoxy-benzyl)-2-aza-bicyclo[3.3.1]non-5-yl]-phenyl}-amide; and 2-Methoxy-ethanesulfonic acid {3-[2-(4-dimethylamino-naphthalen-1-ylmethyl)-2-aza-bicyclo[3.3.1]non-5-yl]-phenyl}-amide and pharmaceutically acceptable salts of said compounds.

22. A pharmaceutical composition comprising an effective amount of a compound according to claim 1 in combination with a pharmaceutically acceptable carrier, excipient or additive.

* * * * *